United States Patent [19]

Barrett et al.

[11] Patent Number: 5,451,683

[45] Date of Patent: * Sep. 19, 1995

[54] SPATIALLY-ADDRESSABLE IMMOBILIZATION OF ANTI-LIGANDS ON SURFACES

[75] Inventors: Ronald W. Barrett, Sunnyvale, Calif.; Michael C. Pirrung, Durham, N.C.; Lubert Stryer, Stanford, Calif.; Christopher P. Holmes, Sunnyvale, Calif.; Steven A. Sundberg, San Francisco, Calif.

[73] Assignee: Affymax Technologies N.V.

[ * ] Notice: The portion of the term of this patent subsequent to Oct. 12, 2010 has been disclaimed.

[21] Appl. No.: 53,124

[22] Filed: Apr. 23, 1993

Related U.S. Application Data

[60] Division of Ser. No. 612,671, Nov. 13, 1990, Pat. No. 5,252,473, which is a continuation-in-part of Ser. No. 435,316, Nov. 13, 1989, abandoned.

[51] Int. Cl.⁶ ................ A61K 31/415; C07D 491/048
[52] U.S. Cl. .................... 548/302.7; 548/303.7; 548/304.1; 548/303.1; 548/323.5; 548/324.5; 548/316.4
[58] Field of Search ............... 548/303.7, 304.1, 303.1, 548/302.7, 323.5, 324.5, 316.4

[56] References Cited

U.S. PATENT DOCUMENTS

| | | | |
|---|---|---|---|
| 4,016,043 | 4/1977 | Schuurs et al. | 195/103.5 |
| 4,130,713 | 12/1978 | Baggiolini et al. | 548/303 |
| 4,371,515 | 2/1983 | Chu | 436/544 |
| 4,542,102 | 9/1985 | Dattagupta et al. | 435/6 |
| 4,557,998 | 12/1985 | Washburn et al. | 430/367 |
| 4,562,157 | 12/1985 | Lowe et al. | 435/291 |
| 4,576,902 | 3/1986 | Saenger et al. | 430/326 |
| 4,582,810 | 4/1986 | Rosenstein | 436/528 |
| 4,656,252 | 4/1987 | Giese | 530/350 |
| 4,709,044 | 11/1987 | Sklavounos | 548/321 |
| 4,719,615 | 1/1988 | Feyrer | 369/284 |
| 4,722,906 | 2/1988 | Guire | 436/501 |
| 4,745,072 | 5/1988 | Ekins et al. | 436/534 |
| 4,762,881 | 8/1988 | Kauer | 525/514.11 |
| 4,775,745 | 10/1988 | Ford et al. | 534/560 |
| 4,895,809 | 1/1990 | Schlabach et al. | 436/518 |
| 4,898,951 | 2/1990 | Symons | 548/303 |
| 5,011,936 | 4/1991 | Kobayashi et al. | 548/316.4 |
| 5,057,612 | 10/1991 | Worley et al. | 548/316.4 |
| 5,086,185 | 2/1992 | Eyer | 548/303 |
| 5,143,854 | 9/1992 | Pirrung et al. | 436/518 |

(List continued on next page.)

FOREIGN PATENT DOCUMENTS

| | | | |
|---|---|---|---|
| 019788 | 5/1980 | European Pat. Off. | C07D 495/04 |
| 127438 | 12/1984 | European Pat. Off. | G01N 33/54 |
| 319957 | 12/1988 | European Pat. Off. | C08J 7/12 |

(List continued on next page.)

OTHER PUBLICATIONS

Takaya et al., 1967, Bull. Chem. Soc. Japan 40: 2636–2640 The preparation of cis-3,4-Ureylenethiophane.

(List continued on next page.)

Primary Examiner—Mary C. Lee
Assistant Examiner—Laura R. Cross
Attorney, Agent, or Firm—Lauren L. Stevens

[57] ABSTRACT

Methods and compositions are described for immobilizing anti-ligands, such as antibodies or antigens, hormones or hormone receptors, oligonucleotides, and polysaccharides on surfaces of solid substrates for various uses. The methods provide surfaces covered with caged binding members which comprise protecting groups capable of being removed upon application of a suitable energy source. Spatially addressed irradiation of predefined regions on the surface permits immobilization of anti-ligands at the activated regions on the surface. Cycles of irradiation on different regions of the surface and immobilization of different anti-ligands allows formation of an immobilized matrix of anti-ligands at defined sites on the surface. The immobilized matrix of anti-ligands permits simultaneous screenings of a liquid sample for ligands having high affinities for certain anti-ligands of the matrix. A preferred embodiment of the invention involves attaching photoactivatable biotin derivatives to a surface. Photolytic activation of the biotin derivatives forms biotin analogs having strong binding affinity for avidin. Biotinylated anti-ligands can be immobilized on activated regions of the surface previously treated with avidin.

21 Claims, 6 Drawing Sheets

U.S. PATENT DOCUMENTS

| | | | |
|---|---|---|---|
| 5,162,352 | 11/1992 | Hall et al. | 514/374 |
| 5,164,407 | 11/1992 | Greenlee et al. | 514/381 |
| 5,171,695 | 12/1992 | Ekins | 436/501 |

FOREIGN PATENT DOCUMENTS

| | | | |
|---|---|---|---|
| 305201 | 3/1989 | European Pat. Off. | C07H 21/00 |
| 0254575 | 1/1998 | European Pat. Off. | G01N 33/543 |
| 615798 | 8/1946 | United Kingdom . | |
| 8901160 | 2/1989 | WIPO | G01N 33/547 |
| 9015070 | 12/1990 | WIPO | C07K 1/04 |
| 9116425 | 10/1991 | WIPO | C12N 11/06 |

OTHER PUBLICATIONS

Takaya et al., 1968, Chem. Abst. 68:29053f. Thiophenes.

Patchornik et al., 21 Oct. 1970, J. Am. Chem. Soc. 92(21):6333–6335 Photosensitive Protecting Groups.

Amit et al., 1974, J. Org. Chem. 39(2):192–196. Photosensitive protecting groups of amino sugars and their use in glycoside synthesis. 2-nitrobenzyloxycarbonylamino and 6-nitroveratryloxcarbonylamino derivatives.

Guire, 1976, Meth. Enz. 1976:280–288 Photochemical Immobilization of Enzymes and Other Biochemicals.

Kohn et al., 1977, J. Org. Chem. 42(6):941–948 Syntheses and Spectral Properties of Substituted Imidazolidones and Imidazolines.

Hofmann et al., 24 May 1978, J. Am. Chem. Soc. 100(11):3585–3590 Avidin–Biotin Affinity Columns. General Methods for attaching biotin to Peptides and proteins.

Hofmann et al., 1982, Biochem. 21:978–984 Avidin binding of carboxyl-substituted biotin and analogues.

Ichimura, 1984, J. Pol. Sci. 22:2817–2828 A convenient photochemical method to immobilize enzymes.

Forster et al., 1985, Nuc. Acids Res. 13(3):745–761 Non-radioactive hybridization probes prepared by the chemical labelling of DNA and RNA with a novel reagent, photobiotin.

Roffman et al., 14 Apr. 1986, Biochem. Biophys. Res. Comm. 136(1):80–85 Selective labeling of functional groups on membrane proteins or glycoproteins using reactive biotin derivatives and 125 I-Streptavidin.

Lacey et al., 1987, Analyt. Biochem. 163:151–158 Photobiotin as a sensitive probe for protein labeling.

Wilchek et al., 1988, Analyt. Biochem. 171:1–32 The avidin–biotin complex in bioanalytical applications.

Ekins, 1989, J. Pharm. Biomed. Anal. 7(2):155–168 Multi-analyte immunoassay.

McCray et al., 1989, Ann. Rev. Biophys. Biophys. Chem. 18:239–270 Properties of uses of photoreactive caged compounds.

Milburn et al., 1989, Biochem. 28:49–55 Synthesis, Photochemistry, and Biological Activity of a Caged Photolabile Acetylcholine Receptor Ligand.

Dower et al., 1991, Ann. Rep. Med. Chem. 26:271–280 Multianalyte microspot immunoassay. The microanalyical 'compact disk' of the future.

Fodor et al., 15 Feb. 1991, Science 251:767–773. Light-directed, spatially addressable parallel chemical synthesis.

Ekins et al., 1992, Ann. Biol. Clin. 50:337–353 Multianalyte microspot immunoassay. The microanalytical 'compact disk' of the future.

Sigrist et al., Sep. 1992, Bio/Technology 10:1026–1028 Light-dependent, covalent immobilization of biomolecules on 'inert' surfaces.

Ekins et al., 1993, Clin. Chem. 39(2):369–370 Multianalyte Testing.

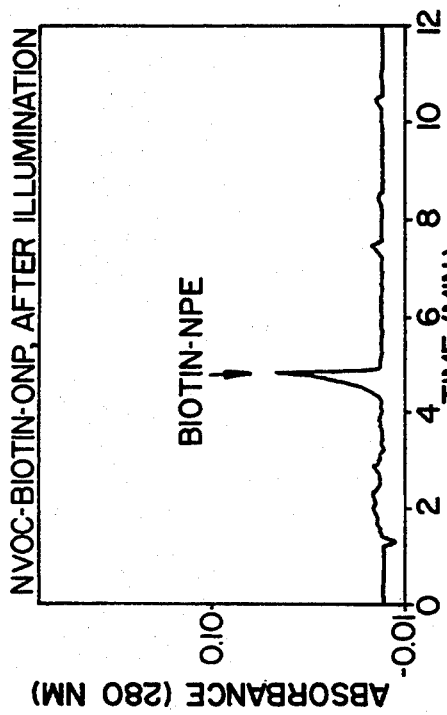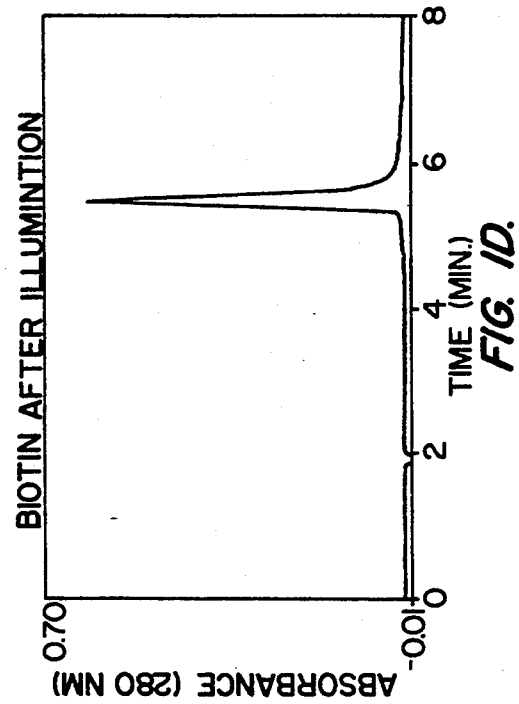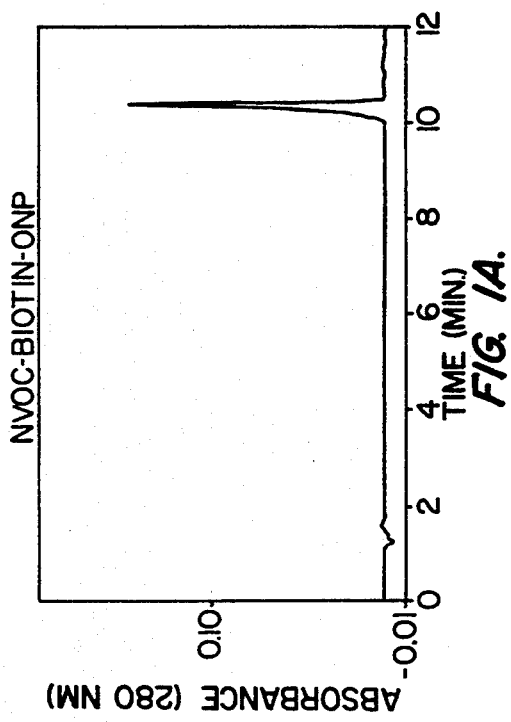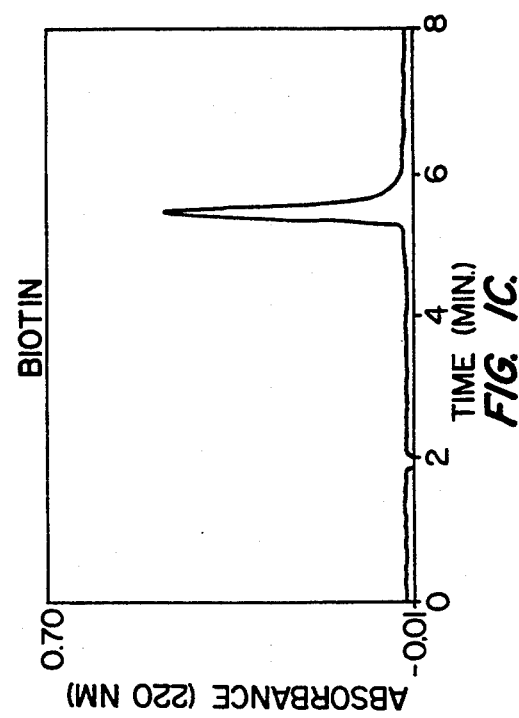

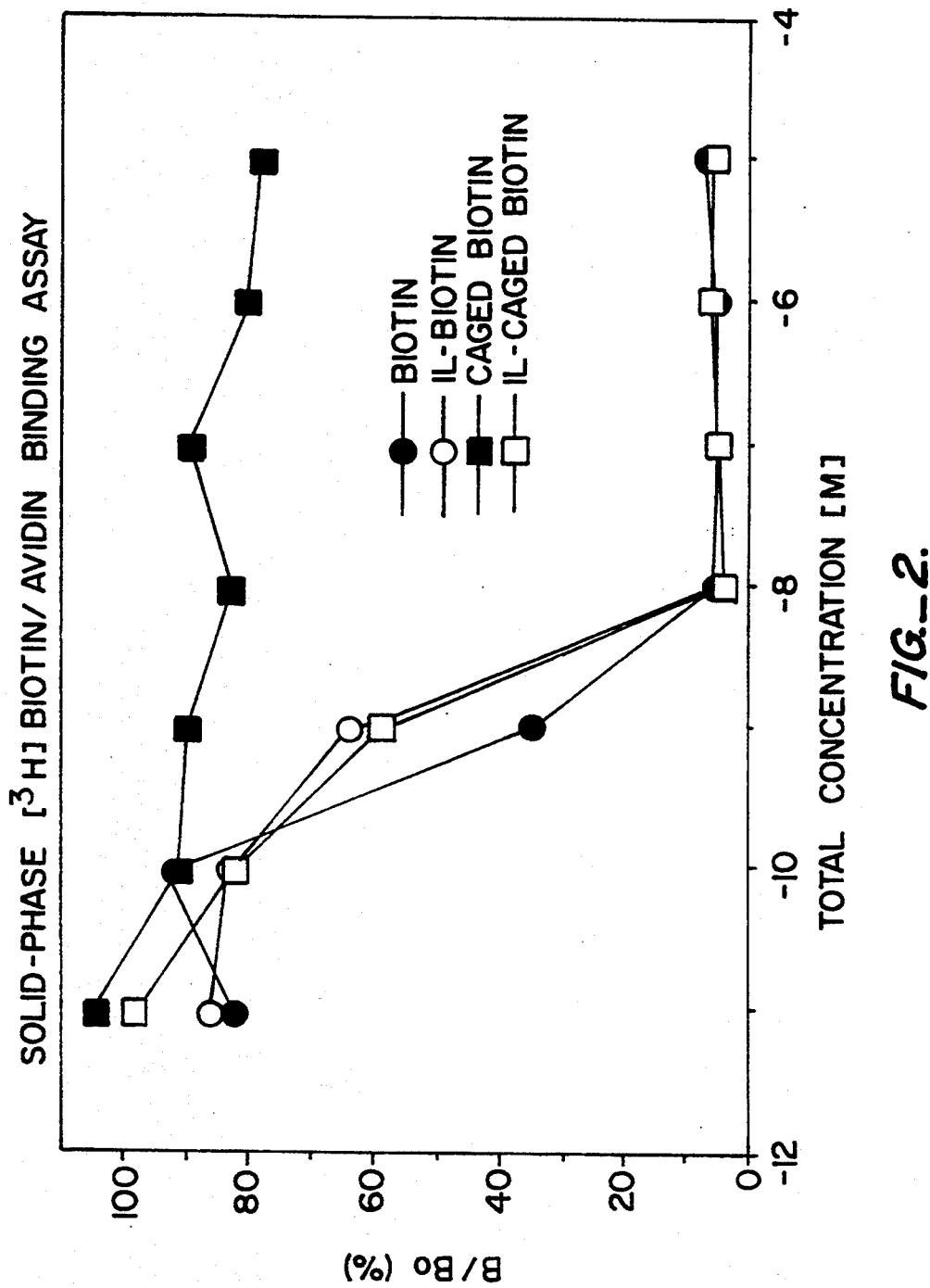
FIG._2.

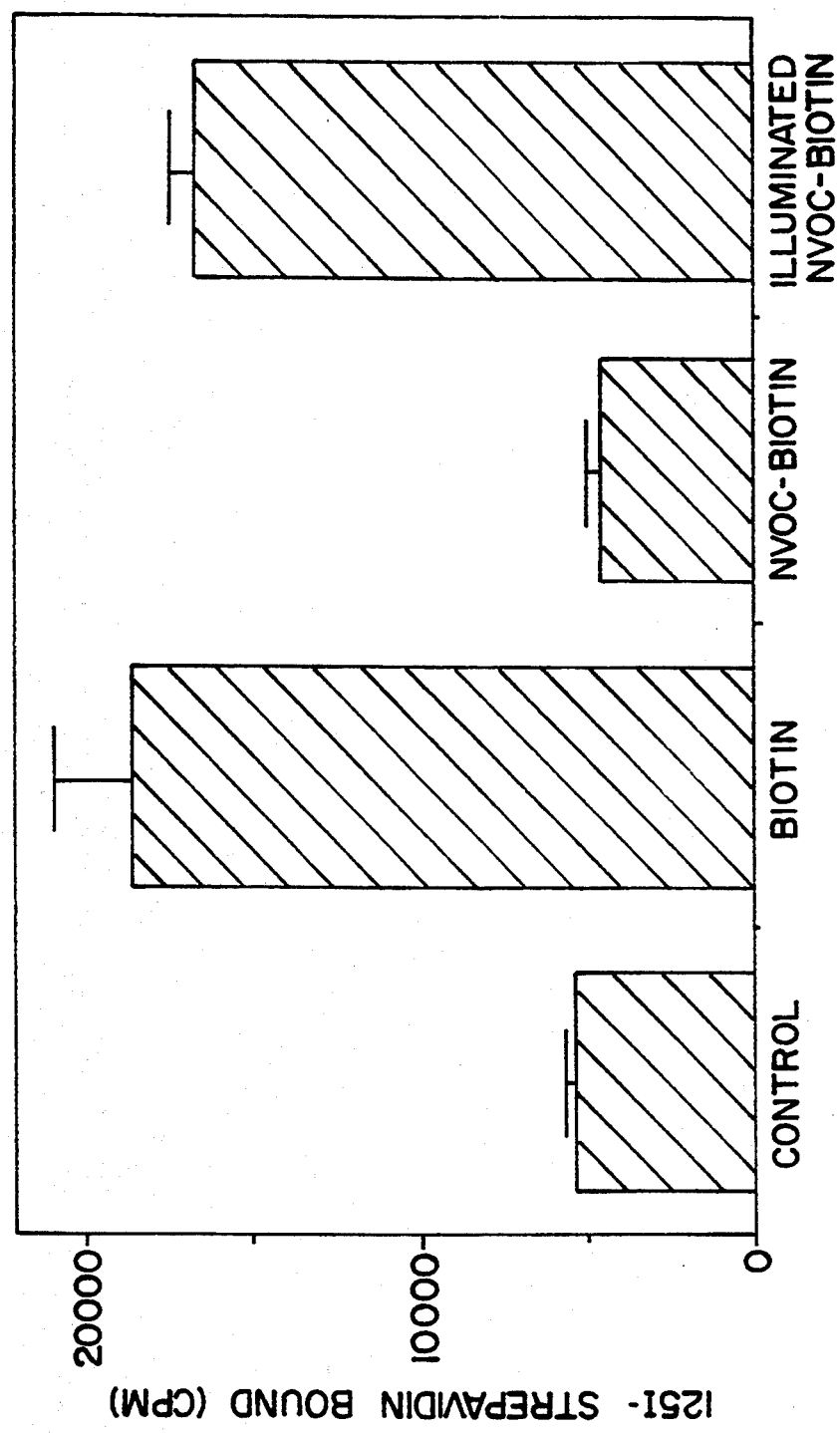
FIG._3.

SPATIALLY-ADDRESSABLE IMMOBILIZATION OF ANTI-LIGANDS ON SURFACES

This is a division of application Ser. No. 07/612,671, filed Nov. 13, 1990, now U.S. Pat. No. 5,252,473 which is a continuation-in-part of application Ser. No. 07/435,316, filed Nov. 13, 1989, now abandoned.

BACKGROUND OF THE INVENTION

The present invention relates generally to methods and compositions useful for immobilizing anti-ligands on surfaces. The immobilized anti-ligands, which can be, for example, hormones or hormone receptors, antibodies or antigens, oligosaccharides, and oligonucleotides, may be used in a variety of screening and assay methodologies for ligands in liquid media.

Certain biological molecules are known to interact and bind to other molecules in a very specific manner. Essentially any molecules having a high binding specificity for each other can be considered a ligand/anti-ligand pair, e.g., a vitamin binding to a protein, a cell-surface receptor binding to a hormone or drug, a glycoprotein serving to identify a particular cell to its neighbors, an IgG-class antibody binding to an antigenic determinant, an oligonucleotide sequence binding to its complementary fragment of RNA or DNA, and the like.

The specific binding properties of anti-ligands for ligands have implications for many fields. For example, the strong binding affinity of antibodies for specific determinants on antigens is critical to the field of immunodiagnostics. Additionally, pharmaceutical drug discovery, in many cases, involves discovering novel drugs having desirable patterns of specificity for naturally-occurring receptors or other biologically important anti-ligands. Many other areas of research exist in which the selective interaction of anti-ligands for ligands is important and are readily apparent to those skilled in the art.

The immobilization of anti-ligands onto surfaces is an important step in performing repetitive assays and screenings of ligands with solid phase systems. Previous methods of attaching anti-ligands to surfaces are limited by low reaction efficiencies or by a general inability to regionally and selectively attach a plurality of anti-ligands to the surface.

A large variety of methods are known for attaching biological molecules to solid supports. See generally, *Affinity Techniques. Enzyme Purification: Part B. Methods in Enzymology*, Vol. 34, ed. W. B. Jakoby, M. Wilchek, Acad. Press, N.Y. (1974) and *Immobilized Biochemicals and Affinity Chromatography, Advances in Experimental Medicine and Biology*, vol. 42, ed. R. Dunlap, Plenum Press, N.Y. (1974), which are incorporated herein by reference. For example, U.S. Pat. No. 4,681,870 describes a method for introducing free amino or carboxyl groups onto a silica matrix. These groups may subsequently be covalently linked to, e.g., a protein or other anti-ligand, in the presence of a carbodiimide. Alternatively, a silica matrix may be activated by treatment with a cyanogen halide under alkaline conditions. The anti-ligand is covalently attached to the surface upon addition to the activated surface. Another example is presented in U.S. Pat. No. 4,282,287, which describes a method for modifying a polymer surface through the successive application of multiple layers of biotin, avidin and extenders. Also, U.S. Pat. No. 4,762,881 describes a method for attaching a polypeptide chain to a solid substrate by incorporating a light-sensitive unnatural amino acid group into the polypeptide chain and exposing the product to low-energy ultraviolet light.

Similarly, a variety of techniques have been developed for attaching oligonucleotides to surfaces. For example, U.S. Pat. No. 4,542,102 describes a method employing a photochemically active reagent (e.g., a psoralen compound) and a coupling agent, which attaches the photoreagent to the substrate. Photoactivation of the photoreagent binds a nucleic acid sequence to the substrate to give a surface-bound probe for a complementary oligonucleotide of the sequence. However, this method has low quantum yields in protic solvents, lacks spatial directability, and relies upon initial affinity between the photoreagent and nucleic acids prior to photoactivation.

U.S. Pat. No. 4,562,157 describes a technique for attaching biochemical ligands to surfaces by attachment of a photochemically reactive arylozide. Irradiation of the azide creates a reactive nitrene which reacts irreversibly with macromolecules in solution resulting in the formation of a covalent bond. The high reactivity of the nitrene intermediate, however, results in both low coupling efficiencies and many potentially unwanted products due to nonspecific reactions.

Thus, there exists a need for improved methods for attaching a broad range of anti-ligands to predefined regions of a solid support surface. The methods should efficiently provide stable attachment of selected anti-ligands to the activated surface regions, yet attachment should be restricted to the activated regions. The present invention fulfills these and other needs.

SUMMARY OF THE INVENTION

Novel methods and compositions of matter are provided for immobilizing anti-ligands on predefined regions of a surface of a solid support. The methods involve attaching to the surface a caged binding member which has a relatively low affinity for other potentially binding species, such as anti-ligands and specific binding substances. The caged binding member is convertible, e.g., by irradiation, to a binding member ultimately capable of immobilizing a desired anti-ligand, preferably via a non-covalent interaction. Predefined regions of the surface are selectively irradiated to convert the caged binding members in the predefined regions to activated binding members. The desired anti-ligands subsequently can be immobilized on the activated regions of the surface.

Importantly, the spatial addressability afforded by the method of the present invention allows the formation of patterned surfaces having preselected reactivities. For example, by using lithographic techniques known in the semiconductor industry, light can be directed to relatively small and precisely known locations on the surface. It is, therefore, possible to activate discrete, predetermined locations on the surface for attachment of anti-ligands. The resulting surface will have a variety of uses. For example, direct binding assays can be performed in which ligands can be simultaneously tested for affinity at different anti-ligands attached to the surface. Ligand binding is detected by a technique such as autoradiography when the ligand is radioactively labelled. Alternatively, fluorescence or other optical techniques can be used. By determining the locations and intensities of labels on the surface it is possible to simultaneously screen ligands for affinity to a plurality of anti-ligands.

A further understanding of the nature and advantages of the invention may be realized by reference to the remaining portions of the specification.

BRIEF DESCRIPTION OF THE DRAWINGS

FIG. 1 presents chromatographic results showing that NVOC-biotin-ONP is converted to biotin-ONP upon illumination in solution.

FIG. 2 presents radioligand binding results showing NVOC-biotin-OMe has low affinity for avidin prior to illumination but high affinity after illumination in solution.

FIG. 3 presents gamma counting results showing that illumination of membrane-bound NVOC-biotin increases the binding of radioactive avidin to the membrane.

Figure 4:
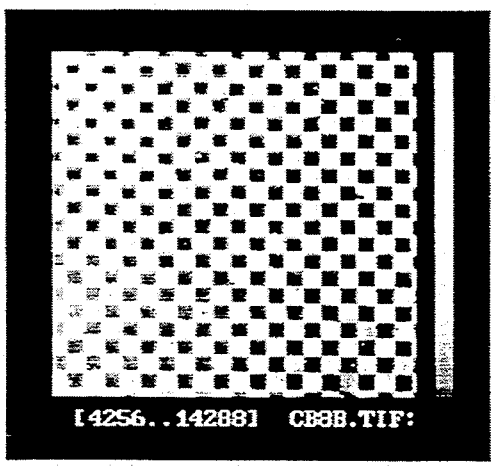
FIG. 4 presents fluorescence results showing the spatial immobilization of Fluorescein-Streptavidin on a biotinylated surface.

DETAILED DESCRIPTION OF THE PREFERRED EMBODIMENTS CONTENTS:

I. Glossary
II. Overview
III. Substrate Preparation
IV. Properties of Binding Members and Caging Groups
   A. Caging Groups
   B. Irradiation of Caged Compounds
V. Attachment of Anti-Ligands
VI. Screenings and Assays
VII. Examples

I. Glossary

The following terms have the following meanings and abbreviations as used herein:

1. Surface (S): A surface is any generally two-dimensional structure on a solid substrate. A surface may have steps, ridges, kinks, terraces and the like without ceasing to be a surface.

2. Predefined Region ($S_i$): A predefined region is a localized area on a surface which is or is intended to be activated. The predefined region may have any convenient shape, e.g., circular, rectangular, elliptical, etc.

3. Crosslinking Group (X): A crosslinking group is a bifunctional chemical entity that serves to connect a binding member to a surface. Usually, crosslinking groups will be heterobifunctional, i.e., they will have different chemical reactivities on either end of the linking group.

4. Binding Member (B): A binding member is any substance having a sufficiently high affinity for another substance. A binding member will have a-sufficiently high affinity for another substance for practice of this invention when it effectively binds the substance without irreversibly separating from it throughout the handling and performance steps of the invention. A binding member is usually, but not always, connected to a surface via a crosslinking group.

5. Caged Binding Member (B*): A caged binding member is a binding member that is provided with a removable (labilizable) chemical protecting group. Such protecting groups are characterized by their abilities to deter effective binding between the binding member to which they are attached and other substances otherwise having affinity for the binding member. Also, the protecting groups are readily labilizable, i.e., they can be detached from the binding member to which they are attached upon exposure to a suitable source of energy.

6. Specific Binding Substance (SBS): A specific binding substance is a compound having a sufficiently high affinity and selectivity for binding to a binding member to permit practice of the present invention. A specific binding substance may be larger or smaller than the binding member to which it specifically binds. The specific binding substance serves as a bridge for attaching an anti-ligand to binding members on the surface.

7. Anti-ligand ($AL_i$): An anti-ligand is a molecule that has a known or unknown affinity for a given ligand and can be immobilized on a predefined region of the surface. Anti-ligands may be naturally-occurring or manmade molecules. Also, they can be employed in their unaltered state or as aggregates with other species. Anti-ligands may be reversibly attached, covalently or noncovalently, to a binding member, either directly or via a specific binding substance. By "reversibly attached" is meant that the binding of the anti-ligand (or specific binding member or ligand) is reversible and has, therefore, a substantially non-zero reverse, or unbinding, rate. Such reversible attachments can arise from non-covalent interactions, such as electrostatic forces, van der Waals forces, hydrophobic (i.e., entropic) forces, and the like. Furthermore, reversible attachments also may arise from certain, but not all covalent bonding reactions. Examples include, but are not limited to, attachment by the formation of hemiacetals, hemiketals, imines, acetals, ketals, and the like (See, Morrison et al., "Organic Chemistry", 2nd ed., ch. 19 (1966), which is incorporated herein by reference). Examples of anti-ligands which can be employed by this invention include, but are not restricted to, cell membrane receptors, monoclonal antibodies and antisera reactive with specific antigenic determinants (such as on viruses, cells or other materials), hormones, drugs, oligonucleotides, peptides, enzymes, substrates, cofactors, lectins, sugars, oligosaccharides, cells, cellular membranes, and organelles.

8. Ligand (L): A ligand is a solvated molecule that is recognized by a particular anti-ligand. Examples of ligands that can be investigated by this invention include, but are not restricted to agonists and antagonists for cell membrane receptors, toxins and venoms, viral epitopes, hormones (e.g., opiates, steroids etc.), hormone receptors, peptides, enzymes, enzyme substrates, cofactors, drugs, lectins, sugars, oligonucleotides, oligosaccharides, proteins, and monoclonal antibodies.

II. Overview

The present invention provides methods for forming predefined regions on a surface of a solid support, wherein the predefined regions are capable of immobilizing anti-ligands. The methods make use of caged binding members attached to the surface to enable selective activation of the predefined regions. The caged binding members are converted to binding members ultimately capable of binding anti-ligands upon selective activation of the predefined regions. The activated binding members are then used to immobilize anti-ligands on the predefined region of the surface. The above procedure can be repeated at the same or different sites on the surface so as to provide a surface prepared with a plurality of regions on the surface containing the same or different anti-ligands. When the anti-ligands have a particular affinity for one or more ligands, screenings and assays for the ligands can be conducted in the regions of the surface containing the anti-ligands.

The present methods are distinguished by the employment of novel caged binding members attached to the substrate. Caged (unactivated) members have a relatively low binding affinity for anti-ligands or specific binding substances when compared with the corresponding affinities of activated binding members. Thus, the binding members are protected until a suitable source of energy is applied to the regions of the surface desired to be activated. Upon application of a suitable energy source, the caging groups labilize, thereby presenting the activated binding member. A typical energy source will be light.

Once the binding members on the surface are activated they may be attached to an anti-ligand. The anti-ligand chosen may be a monoclonal antibody, a nucleic acid sequence, a drug receptor, etc. The anti-ligand will usually, though not always, be prepared so as to permit attaching it, directly or indirectly, to a binding member. For example, a specific binding substance having a strong binding affinity for the binding member and a strong binding affinity for the anti-ligand may be used as a bridge. Alternatively, a covalently-linked conjugate of the specific binding substance and anti-ligand may be used. The method uses an anti-ligand prepared such that the anti-ligand retains its activity toward a particular ligand.

Preferably, the caged binding member attached to the solid substrate will be a photoactivatable biotin analog, i.e., a biotin molecule that has been chemically modified with photoactivatable protecting groups so that it has a significantly reduced binding affinity for avidin or avidin analogs compared to that of natural biotin. In a preferred embodiment, the protecting groups localized in a predefined region of the surface will be removed upon application of a suitable source of radiation to give binding members, that are biotin or a functionally analogous compound having substantially the same binding affinity for avidin or avidin analogs as does biotin.

In another preferred embodiments avidin or an avidin analog will be incubated with activated binding members on the surface until the avidin binds strongly to the binding members. The avidin so immobilized on predefined regions of the surface, can then be incubated with a desired anti-ligand or conjugate of a desired anti-ligand. The multiple biotin binding sites on avidin allow simultaneous binding of biotin attached to the surface and biotin attached to the anti-ligand. The anti-ligand will preferably be biotinylated, e.g., a biotinylated antibody, when avidin is first immobilized on the predefined regions of the surface. Alternatively, a preferred embodiment will present an avidin/biotinylated anti-ligand complex, which has been previously prepared, to activated binding members on the surface.

The following equations depict the best modes of practicing the invention:

The attachment of binding members (B) to a surface (S) of a solid substrate is illustrated by the following reactions:

$$S + B^* \rightarrow S—B^* \text{ or}$$

$$S + B \rightarrow S—B \tag{1}$$

$$S—B + ^* \rightarrow S—B^* \tag{2}$$

where "*" represents a protecting (caging) group. B* is a caged binding member. The protecting groups can either be attached to the binding members once the binding members have been attached to the surface, or more preferably, they will be attached to binding members prior to attaching the binding members to the surface.

Also, surface attachment of binding members can be effected through the use of crosslinking groups (X). This is represented by the following reactions:

$$S + X \rightarrow S—X \tag{1}$$

$$S—X + B^* \rightarrow S—X—B^* \tag{2 or}$$

$$S—X + B \rightarrow S—X—B \tag{2'}$$

$$S—X—B + ^* \rightarrow S—X—B^*$$

The crosslinking groups will usually, though not always, be heterobifunctional chemical species having a first reactivity which permits the crosslinking group to bind readily to the surface and a second reactivity which permits the crosslinking group to bind readily with binding members.

Predefined regions ($S_1$) on the surface can be activated for ultimate immobilization of anti-ligands in the predefined regions by selectively irradiating predefined regions to convert photoactivatable binding members in the predefined region to binding members. This process is illustrated by the following reactions:

$$Si—B^* \xrightarrow{h\nu} Si—B + ^* \text{ or}$$

$$Si—X—B^* \xrightarrow{h\nu} Si—X—B + ^*.$$

The free protecting group, "*" may or may not undergo decomposition reactions. It will usually be washed from the surface, depending upon whether it interferes with subsequent reactions.

Immobilization of anti-ligands ($AL_i$) on predefined regions of the surface can be effected by binding the anti-ligands directly to binding members or through a bridging specific binding substance (SBS). The specific binding substance may be introduced to binding members alone or as a previously prepared conjugate of the anti-ligand. Multiple anti-ligands may be immobilized on the surface when the specific binding substance contains multiple binding sites. Also, it should be noted that an advantage of using a specific binding substance is that an immobilization technique generic for many anti-ligands may be employed. Immobilization of anti-ligands on predefined regions of the surface is illustrated by the following reactions:

$$S_i-X-B+AL_i \rightarrow S_i-X-B-AL_i \text{ or}$$

$$S_i-X-B+SBS-AL \rightarrow S_i-X-B-SBS-AL_i \text{ or}$$

$$S_i-X-B+SBS \rightarrow S_i-X-B-SBS \quad (1)$$

$$S_i-X-B-SBS+AL_i \rightarrow S_i-X-B-SBS-AL_i \quad (2),$$

where the horizontal lines B—SBS, B—$AL_i$, or SBS—$AL_i$ represent bonding between two molecules, preferably a non-covalent bond.

An example of immobilizing a different anti-ligand ($AL_j$) on a different predefined region ($S_j$) of the surface is shown by the equation:

$$S_j-X-B+SBS-AL_j \rightarrow S_j-X-B-SBS-AL_j.$$

Repetition of the above steps on different regions of the surface can produce a matrix of anti-ligands immobilized on the surface. Such a matrix can have any desired pattern of anti-ligands. An example of such a matrix is given below:

$$\begin{array}{ccc} AL_i & AL_j & B^* \\ B^* & B^* & AL_k \\ AL_l & B^* & B^*. \end{array}$$

An immobilized anti-ligand on a surface will have a specific binding affinity for a particular ligand (L). An example of a direct assay on a predefined region of the surface for the presence of a labeled ligand (L') in a liquid medium is illustrated by the following reaction:

$$S_i-X-B-SBS-AL_i+L' \rightarrow S_i-X-B-SB-S-AL_i-L'.$$

The resulting surface can be washed free of unbound ligand and analyzed for the presence of label. The labels will serve as markers localized at the predefined regions on the surface corresponding to the presence of anti-ligands for the ligand at those predefined regions.

Some examples of competitive assays, in which a target ligand (L) "competes" with another ligand (L') for a site on the surface, are illustrated by the following reactions:

$$S_i-X-B-SBS-AL_i-L'+L \rightarrow S_i-X-B-SB-S-AL_i-L+L' \quad (1).$$

$$S_i-X-B-SBS-AL_i+L/L' \rightarrow S_i-X-B-SB-S-AL_i-L'+L \quad (2).$$

The presence of target ligand can be determined by analyzing appropriately for the loss or buildup of label on the predefined regions of the surface.

III. Substrate Preparation

Essentially, any conceivable solid substrate may be employed in the invention. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate and its surface preferably form a rigid support on which to carry out the reactions described herein. The substrate and its surface should also be chosen to provide appropriate light-absorbing characteristics. For instance, the substrate may be a polymerized Langmuir Blodgett film, functionalized glass, Si, Ge, GaAs, GaP, $SiO_2$, $SIN_4$, modified silicon, or any one of a wide variety of polymers such as (poly)tetrafluoroethylene, (poly)vinylidenedifluoride, or combinations thereof. Other substrate materials will be readily apparent to those of skill in the art upon review of this disclosure. In a preferred embodiment the substrate is flat glass or single-crystal silicon with surface features of less than 10 Å.

Surfaces on the solid substrate will usually, though not always, be composed of the same material as the substrate. Thus, the surface may be composed of any of a wide variety of materials, for example, polymers, plastics, resins, polysaccharides, silica or silica-based materials, carbon, metals, inorganic glasses, membranes, etc., provided only that caged binding members can be attached firmly to the surface of the substrate. Preferably, the surface will contain reactive groups, which could be carboxyl, amino, hydroxyl, or the like. Most preferably, the surface will be optically transparent and will have surface Si—OH functionalities, such as are found on silica surfaces.

The surface of the substrate is preferably provided with a layer of crosslinking groups, although it will be understood that the crosslinking groups are not required elements of the invention. The crosslinking groups are preferably of sufficient length to permit binding members on the surface to interact freely with compounds in solution. Crosslinking groups may be selected from any suitable class of compounds, for example, aryl acetylenes, ethylene glycol oligomers containing 2-10 monomer units, diamines, diacids, amino acids, or combinations thereof. Other crosslinking groups may be used in light of this disclosure.

Crosslinking groups may be attached to the surface by a variety of methods which are readily apparent to one having skill in the art. For example, crosslinking groups may be attached to the surface by siloxane bonds formed via reactions of crosslinking groups bearing trichlorosilyl or trisalkoxy groups with hydroxyl groups on the surface of the substrate. Preferably, the crosslinking group used with a glass surface is N-BOC-aminopropyltriethoxy silane. The crosslinking groups may optionally be attached in an ordered array, i.e., as parts of the head groups in a polymerized Langmuir Blodgett film. Clearly, the type of crosslinking group selected, and the method selected for attaching it to the surface, will depend primarily on the crosslinking group having suitable reactivity with the binding member desired to be attached to the surface.

Additional length may be added to the crosslinking groups by the addition of single or multiple linking groups. Such linking groups are preferably heterobifunctional, having one end adapted to react with the crosslinking groups and the other end adapted to react with the binding member or another linking group. The linking groups may be attached by a variety of methods which are readily apparent to one skilled in the art; for instance, esterification or amidation reactions of an activated ester of the linking group with a reactive hydroxyl or amine on the free end of the crosslinking group. A preferred linking group is N-BOC-6-aminocaproic acid (i.e., N-BOC-6-aminohexanoic acid) attached by the BOP-activated ester. After deprotection to liberate the free amine terminus, another N-BOC-aminocaproic linker can be added. Attachment of crosslinking and linking groups to caged binding members are discussed more fully below.

Many methods are available for immobilizing the binding members of the present invention on surfaces. The binding members may be linked to the surface in their active forms, and later provided with protecting (caging) groups. More preferably, binding members will be provided in their protected forms. The method chosen for linking binding members to the surface will depend upon the chemical properties of the binding member selected for attachment to the surface. A preferred method for immobilizing the binding members of the present invention involves chemical derivatization or activation of the caged binding member prior to attachment to the surface or linker. This derivative or activated species is then reacted with functionalities on the substrate to give the desired linkage. For example, one method for attaching a binding member to a surface employs a heterobifunctional crosslinking reagent, such as diepoxide, which both activates the surface and provides a group that reacts with an activated binding member. Alternatively, the surface can be activated with cyanogen bromide. Reaction with a binding member containing a terminal amino group permits attachment of the binding member to the surface. (U.S. Pat. No. 4,542,102). In the presence of a carbodiimide or other activating agent, for example, the amine group can be coupled to the carboxyl terminus of a binding member desired to be immobilized on the surface.

A preferred embodiment of the present invention involves attaching "caged" derivatives of biotin or biotin analogs to a glass surface. Caged biotin may be attached to the surface through strong noncovalent interactions, e.g., by crosslinking via a suitable linker to another biotin molecule and reacting with a surface to which avidin has been attached, or alternatively, and preferably, by covalent attachment to the surface. The latter may be accomplished by derivatizing caged-biotin and biotin analogues at their carboxylic acid terminus. Many biotin derivatives have been described previously. For example, the surface can be provided with biotin anti-ligands, e.g., antibiotin antibodies, which specifically bind the carboxyl arm of biotin without interfering with the avidin-binding ureido ring of biotin.

Still another method for immobilizing the caged binding members of the present invention involves chemical derivatization or activation of the binding member prior to attachment to the surface or linker. For example, when the surface is a polymer containing primary amines and biotin is selected as the binding member, the N-hydroxysuccinimide ester derivative of biotin can react with the surface to give a biotin-surface complex (U.S. Pat. No. 4,282,287).

Alternatively, and preferably, photoactivatable biotin and biotin analog derivatives will be covalently attached to the surface. To effect this transformation, the biotin and biotin analogs may be derivatized at their carboxylic acid terminus. Many biotin derivatives have been described previously involving derivatization at the free carboxyl end of biotin. See, e.g., Bayer et al., *Methods of Biochemical Analysis*, vol. 26 (D. Glick, ed.), 1–45 (1980), which is incorporated herein by reference. For example, photoactivatable biotin derivatives may be reacted, in the presence of an activating reagent, such as a carbodiimine or BOP, with the amine groups of crosslinking groups previously immobilized on the surface to give the biotin attached to the surface via an amide linkage. The active ureido ring of biotin, either free or protected, is located far enough away from the site of attachment that, when unprotected, binding with avidin is not significantly diminished.

It should be appreciated that the above discussion of exemplary surface attachment reactions is only illustrative of the general method for attaching caged binding members to a surface and should not be regarded in any way as limiting the applicability of the method to biotin, biotin analogs, or specific crosslinking groups. Other types of binding members also amenable to the above attachment techniques include enzymes, antibodies, oligonucleotides and the like and are readily apparent to one skilled in the art.

IV. Properties of Binding Members and Caging Groups

The present method permits use of a wide variety of caged binding members to effect the immobilization of anti-ligands on the surface. The method is generally applicable to such classes of compounds as enzymes, substrates, cofactors, immunoglobulins, antibodies, haptens, antigens, oligonucleotides, oligosaccharides, lectins, proteins, glycoproteins, etc., being the binding member provided that the selected derivative of such species is activatable upon exposure to a suitable energy source. Moreover, the binding member can possess a multiplicity of binding sites for an anti-ligand or specific binding substance.

The binding member selected will have a high binding affinity either for an anti-ligand or a specific binding substance. Preferably, a specific binding substance will provide a link between the binding member and the anti-ligand. Usually, the interactions between a binding member and a specific binding substance and an anti-ligand or anti-ligand conjugate will be noncovalent in nature. When a specific binding substance provides a link between the binding member and the anti-ligand, the specific binding substance will be connected to the anti-ligand either covalently or through noncovalent interactions.

The binding member on a surface must have a strong affinity for an anti-ligand or specific binding substance to prevent migration or loss of the anti-ligand during wash steps. The affinity between the binding member and an anti-ligand or a specific binding substance is best represented by the off-rate of anti-ligand or specific binding substance from a binding member. However, off-rates often are not conveniently known or determined. Therefore, binding affinity may also be represented by the affinity constant ($K_a$) for equilibrium concentrations of associated and dissociated configurations, i.e., $K_a = [\text{B-SBS}]/[\text{B}][\text{SBS}]$, where [B], [SBS] and [B-SBS] are represented by the affinity constant ($K_a$)

for equilibrium concentrations of associated and dissociated configurations, the concentrations of the binding member (B), the concentration of specific binding substance (SBS), and the concentration of associated complex (B—SBS), respectively, at equilibrium. An analogous definition of K, applies when SBS is replaced with an anti-ligand (AL) or a specific binding substance—anti-ligand conjugate (SBS—AL), etc. The affinity constants of some sample classes of compounds suitable for use in the present invention are presented in Table 1.

TABLE 1

Affinities of Sample Binding Members and Specific Binding Substances (SBS).

| Binding Member | SBS | Affinity ($K_a$ $M^{-1}$) |
| --- | --- | --- |
| Membrane sites | Lectins | $10^{6-7}$ |
| Haptens | Antibodies | $10^{5-11}$ |
| Antigenic determinants | Antibodies | $10^{5-11}$ |
| Biotin | Avidin | $10^{15}$ |
| Iminobiotin | Avidin | $10^{11}$ |
| 2-thiobiotin | Avidin | $10^{13}$ |
| Dethiobiotin | Avidin | $10^{13}$ |
| 1'-N-methoxy-carbonylbiotin methyl ester | Avidin | $10^{7}$ |
| 3'-N-methoxy-carbonylbiotin methyl ester | Avidin | $10^{9}$ |

*References: U.S. Pat. No. 4,282,287; Green, "Avidin" in Advances in Protein Chemistry, Academic Press, vol. 29, 105 (1975).

Preferably, the affinity constant between the activated binding member and another species, i.e., a specific binding species, an anti-ligand, or anti-ligand conjugate, will be greater than about $10^7$ $M^{-1}$. More preferably, the $K_a$ will be greater than about $10^{11}$ $M^{-1}$, and most preferably, the $K_a$ will be about $10^{15}$ $M^{-1}$ or greater. Likewise, when a specific binding substance is used, the affinity constant between the specific binding substance and an anti-ligand or anti-ligand conjugate will have substantially the same ranges as given above.

An activated (uncaged) binding member is considered to have a relatively strong (high) binding affinity for another species, i.e., a specific binding substance, an anti-ligand, or a conjugate of an anti-ligand, when the $K_a$ between the binding member and the other species is at least about three orders of magnitude greater than the corresponding $K_a$ between the caged binding member and the other species. Similarly, a caged binding member is considered to have a relatively low binding affinity for another species, i.e., specific binding substance, anti-ligand or anti-ligand conjugate, when the $K_a$ between the caged binding member and the other species is about three orders of magnitude less than the corresponding $K_a$ for the activated binding member. Preferably, the affinity constant for the caged binding member will be at least five orders of magnitude lower than the corresponding activated binding member's affinity constant. Most preferably, the binding constant for the caged binding member will be even lower, e.g., seven orders of magnitude lower, than the corresponding activated binding member's affinity constant. However, the suitability of a given caged binding member/binding member pair for practice of the invention is determined ultimately by whether the selected pair permits proper operation of the invention.

A preferred embodiment of the present invention employs biotin and biotin analogs as the binding members. Typical biotin analogs include dethiobiotin, iminobiotin, 2-thiobiotin, azabiotin, biocytin, and biotin sulfone, and other compounds readily apparent to one skilled in the art. Exemplary biotin analogs include, but are not limited by, those presented in Table 2. Other biotin analogs are presented in N. Green, "Avidin" in Advances in Protein Chemistry, Vol. 29, Acad. Press, p. 85-133 (1975), which is incorporated by reference herein. Biotin analogs include compounds and structures in which biotin is bound to another species, such as a surface, as long as the analog has a binding affinity for avidin that is similar to that of biotin. The biotin or biotin analogs may be subsequently reacted with avidin compounds, streptavidin, and analogues thereof.

Typical examples of avidin and avidin analogs include, but are not limited to, the avidin found in eggs and streptavidin. Streptavidin is a typical example of an avidin analog and is a bacterial biotin-binding protein which has physical characteristics similar to those of egg avidin, despite considerable differences in composition.

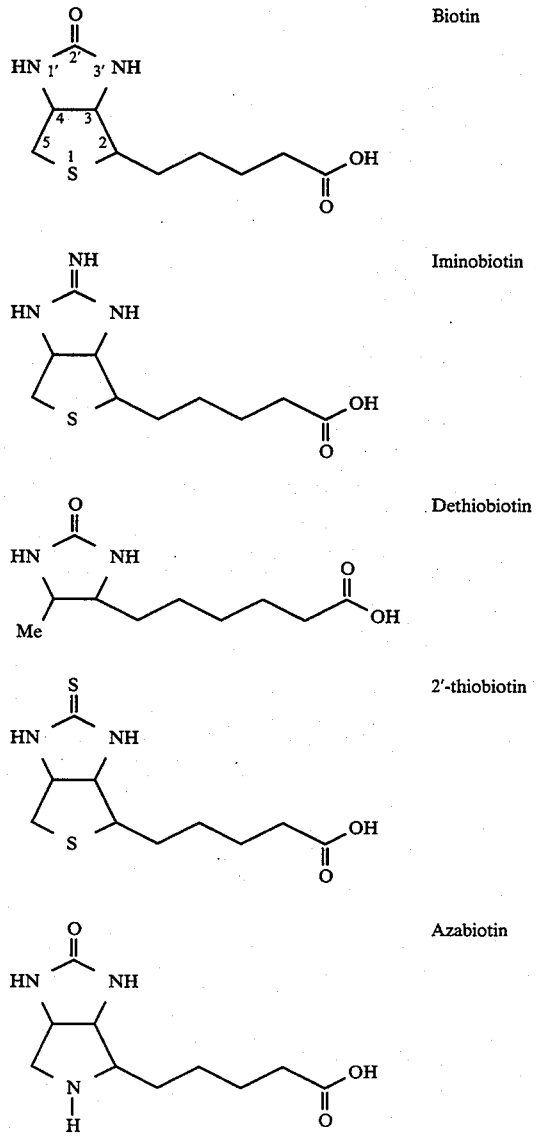

TABLE 2

TABLE 2-continued

| Biotin and Biotin Analogs | Name |
|---|---|
| (structure) | Bisnorazabiotin |

Reference: N. Green, "Avidin," in Advances in Protein Chemistyr, Vol. 29, Academic Press, p. 85-133 (1975).

Binding members other than biotin and their corresponding specific binding substances may be employed in the present invention. By way of example and not limitation, some alternative embodiments of the invention follow:

1. Caged Cyclic AMp/Anti-cAMP Antibodies

High-affinity polyclonal antibodies to cAMP are produced by immunizing with 2'O-monosuccinyl adenosine 3',5' cyclic monophosphate conjugated to a protein such as bovine serum albumin or thyroglobulin. Purified polyclonal antibodies been conjugated. The $K_a$ of polyclonal antibodies to cAMP is in are prepared by affinity chromatography using agarose gel to which 2'O-monosuccinyl adenosine 3',5' cyclic monophosphate has been conjugated. The $K_a$ of polyclonal antibodies to cAMP is in the range of $10^{10}$ to $10^{12}$ $M^{-1}$.

A photoactivatable analog of cAMP has been previously described (Nerbone et al., Nature (1984) 310:74). It is unlikely that polyclonal antibodies against cAMP have high affinity for the photoactivatable analog of cAMP. If the polyclonal antibodies should cross-react with the photoactivatable analog of cAMP, monoclonal antibodies can be produced which discriminate between cAMP and the photoactivatable cAMP analog.

The 2'O-monosuccinyl derivative of the photoactivatable cAMP analog is attached to a surface through the free carboxyl of the succinyl group as described above. Specific regions of the surface are illuminated resulting in the removal of the protecting group from the cAMP. Anti-ligands which have been conjugated to anti-cAMP antibodies are reacted with the surface. The anti-ligands are immobilized only at the predefined regions of the surface that were illuminated.

2. Caged Tetrahydrofolate/Folate Binding Proteins

N5-(Nitroveratryloxycarbonyl)tetrahydrofolate is activated at its glutamyl gamma-carboxylate with a carbodiimide reagent and coupled to an amino-derivatized surface. Desired predefined regions on the surface are irradiated with light suitable for deprotection of the NVOC group. In the illuminated regions, the NVOC group is removed to produce tetrahydrofolate bound to the surface. High-affinity folate binding proteins derived from human erythrocyte membranes (Antony et al., J. Clin. Invest. (1987) 80:711-723; $K_a=3\times10^{11}$ $M^{-1}$ for tetrahydrofolate), crosslinked to a desired anti-ligand, are then immobilized on the selected regions of the surface.

3. Caged Mannose/Concanavalin A

8'-(Trichlorosilyl)octyl 6-(nitroveratryloxy)-a-D-mannoside is covalently attached to a silica or glass surface by methods well-known to those skilled in the art. Predefined regions of the surface are irradiated with light suitable for deprotection of the nitroveratryloxy group. In the irradiated regions, the protecting group is removed to produce octyl-α-D-mannoside bound to the surface. In unexposed areas, the 6-(nitroveratryloxy) group protects the mannoside from binding to the lectin. Concanavalin A, conjugated to a desired anti-ligand, is added to the surface and binds to those mannose units on the surface that have been deprotected. The anti-ligand is thereby immobilized on the desired regions of the surface.

The above modes for practicing the invention are examples only. Those skilled in the art will recognize that any pair of (i) binding member and specific binding substance, (ii) binding member and anti-ligand or anti-ligand conjugate, or (iii) specific binding substance and anti-ligand or anti-ligand conjugate may be used. The only restrictions on the choice of binding member, specific binding substance and anti-ligand or anti-ligand conjugate are that: (1) the binding member has a high affinity for the specific binding substance, anti-ligand or anti-ligand conjugate selected, (2) the binding member can be "caged" with a removable protecting group, and (3) the caged binding member has a relatively low affinity for specific binding substances, anti-ligands, or anti-ligand conjugates, and any species which interfere with practice of the invention.

A. Caging Groups

Many different protecting (caging) groups can be employed for modifying binding members to give the caged binding members of the present invention. The protecting groups should be sterically large enough to reduce the affinity of the binding member for anti-ligands or specific binding substances to permit operability of the invention, although protecting groups utilizing other types of interactions, such as electronic (i.e., Van der Waals), hydrophobic, etc., could be used. The selection of suitable caging groups will depend upon the size and chemical nature of the binding member chosen and will be readily apparent to one skilled in the art.

In a preferred embodiment, the caging groups will be photoactivatable. The properties and uses of photoreactive caged compounds have been reviewed. See, J. McCray, et al., Annu. Rev. Biophys., Biophys. Chem., 18: 239-70 (1989), which is incorporated herein by reference. Preferably, the photosensitive cages will be activatable by low energy ultraviolet or visible light. In some embodiments, however, activation may be performed by the methods discussed later, including localized heating, electron beam techniques, laser pumping, and oxidation or reduction with microelectrodes. Alternatively, the reactive group may be activatable by electron beam lithography, X-ray lithography, or any other radiation. Suitable reactive groups for electron beam lithography include sulfonyl compounds. Other methods may be used including, for example, exposure to an electric current source, preferably using microelectrodes directed to the predefined regions of the surface which are desired for activation. Other reactive groups and methods of activation may be used in light of this disclosure.

A further preferred embodiment of the present invention employs photoactivatable N-derivatives of biotin and biotin analogs to reduce the natural affinity of biotin for other compounds, such as avidin used as a specific binding substance, until the groups attached to the N-positions are photoremoved. A few references describe N-derivatization of biotin and biotin analogs. See, Kohn et al., *J. Org. Chem.* (1977) 42:941–948, and Knappe et al., *Biochemische Zeitschrift*, 335, 168–176 (1961). However, none of these references provide photoactivatable biotin derivatives. The use of a photosensitive biotin derivative, photobiotin, has been previously described for labelling proteins and nucleic acids. Lacey, E. *Anal, Biochem.*, 163:151–8 (1987); Forster, A. C. *Nucleic Acids Res.*, 13:745–61 (1985). However, photobiotin is a derivative of the carboxylate terminus of biotin, which is located away from the recognition site and, hence, does not significantly reduce binding to avidin or streptavidin.

Many, although not all, of the photosensitive protecting groups will be aromatic compounds. Suitable photoremovable protecting groups are described in, for example, McCray, et al., Patchornik, *J. Am. Chem. Soc.* (1970) 92:6333 and Amit, et al., *J. Org. Chem.* (1974) 39:192, which are incorporated herein by reference. See, also, *Calbiochem Catalog*, (San Diego, Calif., 1989), p. 244–247. More preferably, the photosensitive group will be a nitro benzylic compound, such as o-nitrobenzyl or benzylsulfonyl groups. In a preferred embodiment, 6-nitroveratryloxycarbonyl (NVOC) and its derivatives, such as 6-nitropiperonyloxycarbonyl (NPOC), α,α-dimethyl-dimethoxybenzyloxycarbonyl (DDZ) or 1-pyrenylmethyl may be employed.

When the selected binding member is biotin or a biotin analog, photosensitive protecting groups may be provided at the N-1', N-3' or to an oxygen, imino, or sulfur group at the 2'-C position of the ureido ring. When the protecting group is attached to a 2'—C—O— position, the group will preferably be an o-nitro benzylic group having a hydrogen atom at the alpha benzylic position. In such case, the biotin or biotin residue is an imidazolidine group. When the protecting group is attached to a 1'—N or 3'—N atom, the protecting group will preferably be an o-nitro benzylic group having a hydrogen atom bound to the alpha carbon atom and optionally an oxycarbonyl group linking the alpha carbon atom through the oxygen atom. In the latter case, the derivatized nitrogen atom of the imidazolidone group will be bound to the carbon atom of the oxycarbonyl group.

A preferred embodiment of the invention has the following formula:

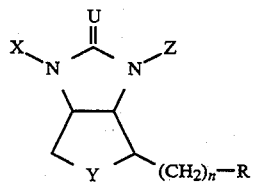

where X and Z are hydrogen, or oxycarbonyls of lower alkyl, aryl, or benzyl groups, provided that X and Z are not both hydrogen: R is hydrogen, lower alkyl, aryl, carboxylate, alkyl formate, aryl formate, formamide, N-alkylformamide, N-succinimidyl, hydroxyl, alkoxyl, thiol, thioether, disulfide, hydrazide or an amine group; U is O, S, or NH; Y is sulfur, oxygen, methylene, carbonyl, or a sulfinyl, or sulfonyl group, or Y represents two hydrogen atoms attached to the respective carbons; and n=0–7. Also, inorganic and organic acid addition salts of the above compounds can be employed. Furthermore, R can represent a surface or a surface provided with a suitable crosslinking group. In another preferred embodiment, R is hydrogen, lower alkyl, aryl, carboxylate, alkyl formate, aryl formate, formamide, N-alkylformamide, N-succinimidyl, hydroxyl, alkoxyl, thiol, thioether, disulfide, hydrazide or an amine group connected to a linking group of a suitable length, such as monomer, dimer, trimer, or oligomer of 6-aminocaproic acid, an oligomer of ethylene glycol having up to 10 units dioxadodecane-propyl, or other suitable linkers. A more preferred embodiment is when R is methyl formate or p-nitrophenyl formate. A further preferred embodiment is when U is O, Y is S, and n=4. A preferred embodiment is when Y represents two hydrogen atoms attached to respective carbons, which eliminates the lower ring leaving a methyl group and a hexanoic acid group:

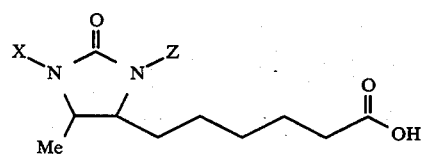

A further preferred embodiment is when X or Z is a nitro aromatic compound containing a benzylic hydrogen ortho to the nitro group. A still further preferred embodiment is when X or Z has the formula:

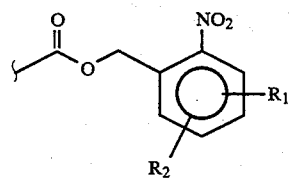

where $R_1$ and $R_2$ are hydrogen, lower alkyl, aryl, benzyl, halogen, hydroxyl, alkoxyl, thiol, thioether, amino, nitro, carboxyl, formate, sulfonate, formamido or phosphido groups. A further preferred embodiment is when X or Z is a nitroveratryloxycarbonyl group.

Most preferred embodiments are when X is 6-nitroveratryloxycarbonyl, Z is hydrogen, and R is methyl formate or p-nitrophenyl formate.

Another preferred embodiment is when X or Z is a ring-disubstituted benzyloxycarbonyl group having the formula:

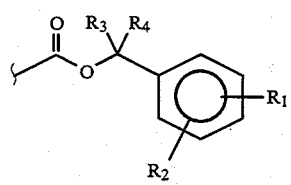

where $R_1$ and $R_2$ are hydrogen, lower alkyl, aryl, benzyl, pyrenyl, halogen, hydroxyl, alkoxyl, thiol, thioether, amino, nitro, carboxyl, formate, formamido or phosphido groups, and $R_3$ and $R_4$ are hydrogen, lower alkyl, aryl, benzyl, halogen, hydroxyl, alkoxyl, thiol, thioether, amino, nitro, carboxyl, formate, formamido or phosphido groups. More preferably $R_1$ and $R_2$ are methoxy groups. More preferably $R_3$ and $R_4$ are methyl groups. A most preferred embodiment is when $R_1$ and $R_2$ are methoxy groups and $R_3$ and $R_4$ are methyl groups.

A further preferred embodiment is when X has the formula:

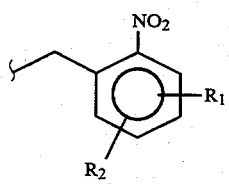

where $R_1$ and $R_2$ are hydrogen, lower alkyl, aryl, benzyl, halogen, hydroxyl, alkoxyl, thiol, thioether, amino, nitro, carboxyl, formate, formamido or phosphido groups. A still further preferred embodiment is when X is a nitroveratryl group.

Most preferred embodiments are when X is 6-nitroveratryl, U or W is hydrogen, and R is methyl formate or p-nitrophenyl formate.

A further preferred embodiment is when X is a ring-disubstituted benzyl group. A more preferred embodiment is when the ring-disubstituted benzyl group has the formula:

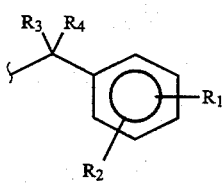

where $R_1$, $R_2$, $R_3$, and $R_4$ are hydrogen, lower alkyl, aryl, benzyl, halogen, hydroxyl, alkoxyl, thiol, thioether, amino, nitro, carboxyl, formate, formamido or phosphido groups. Most preferred embodiments are when $R_1$ and $R_2$ are methoxy and $R_3$ and $R_4$ are methyl.

Another preferred embodiment is when the composition has the formula selected from the group consisting of:

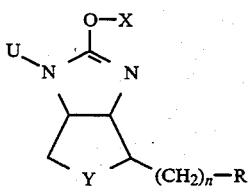

and

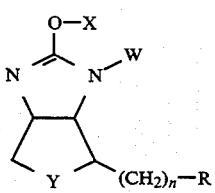

wherein X is selected from the group consisting of
(a) hydrogen,
(b) lower alkyl,
(c) aryl,
(d) benzyl,
(e) substituted benzyl selected from the group consisting of

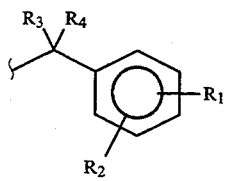

wherein $R_1$, $R_2$, $R_3$ and $R_4$ are selected from the group consisting of hydrogen, lower alkyl, aryl, benzyl, halogen, hydroxyl, alkoxyl, thiol, thioether, amino, nitro, carboxyl, formate, formamido and phosphido groups provided that $R_1$, $R_2$, $R_3$ and $R_4$ are not all hydrogen, and

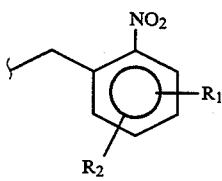

wherein $R_1$ and $R_2$ are selected from the group consisting of hydrogen, lower alkyl, aryl, benzyl, halogen, hydroxyl, alkoxyl, thiol, thioether, amino, nitro, carboxyl, formate, formamido and phosphido groups.
(f) nitroveratryl,
(g) 6-nitroveratryl.
(h) 6-nitroveratryloxycarbonyl and
(i) 6-nitropiperonyloxycarbonyl where U or W is hydrogen;
U and W are selected from the group consisting of hydrogen, lower alkyl, aryl, benzyl and substituted benzyl selected from the group consisting of

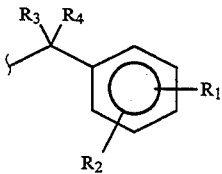

wherein $R_1$, $R_2$, $R_3$ and $R_4$ are selected from the group consisting of hydrogen, lower alkyl, aryl, benzyl, halogen, hydroxyl, alkoxyl, thiol, thioether, amino, nitro, carboxyl, formate, formamido and phosphido groups provided that $R_1$, $R_2$, $R_3$ and $R_4$ are not all hydrogen, and

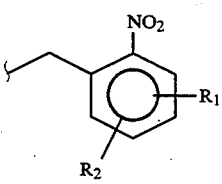

wherein $R_1$ and $R_2$ are selected from the group consisting of hydrogen, lower alkyl, aryl, benzyl, halogen, hydroxyl, alkoxyl, thiol, thioether, amino, nitro, carboxyl, formate, formamido and phosphido groups, provided that only one of U or W is present;
R is selected from the group consisting of hydrogen, lower alkyl, aryl, carboxylate, alkyl formate, aryl formate, formamide, N-alkyl formamide, N-succinimidyl, hydroxyl, alkoxyl, thiol, thioether, disulfide, hydrazide and amine groups;

Y is selected from the group consisting of sulfur, oxygen, methylene, carbonyl, sulfinyl and sulfonyl groups, or Y represents two hydrogens attached to the respective carbons; and n=0-7. Also, inorganic and organic acid addition salts of the above compound are suitable. A more preferred embodiment is when Y is sulfur and n=4.

Clearly, many photosensitive protecting groups are suitable for use in the present inventive methods. Some examples of acceptable photosensitive protecting groups are presented in Table 3. Also, some example protecting groups and their corresponding wavelengths for deprotection are provided in Table 4.

TABLE 3

| Example Protecting Groups | Name |
| --- | --- |
| [structure] | 6-nitroveratryloxycarbonyl (NVOC) |
| [structure] | dimethyldimethoxybenzyloxycarbonyl (DDZ) |
| [structure] | 2-nitrobenzyloxycarbonyl (NBOC) |
| [structure] | 5-bromo-7-nitroindolinyl (BNI) |
| [structure] | O-hydroxy-α-methyl-cinnamoyl (HMC) |
| [structure] | 2-oxymethylene anthraquinone (OMA) |

TABLE 4

Example protecting groups and their deprotection wavelengths

| Group | Deprotection Wavelength |
| --- | --- |
| Nitroveratryloxycarbonyl | UV (300–350 nm) |
| Nitrobenzyloxycarbonyl | UV (300–350 nm) |
| Dimethyldimethoxybenzyloxycarbonyl | UV (280–300 nm) |
| 5-Bromo-7-nitroindolinyl | UV (420 nm) |
| o-Hydroxy-α-methyl cinnamoyl | UV (300–350 nm) |

TABLE 4-continued

Example protecting groups and their deprotection wavelengths

| Group | Deprotection Wavelength |
| --- | --- |
| 2-Oxymethylene anthraquinone | UV (350 nm) |

B. Irradiation

Once the surface is covered with a plurality of caged binding members, selected regions of the surface may be irradiated to provide activated binding members. Predefined regions of the surface may be selectively activated by electron beam lithography, ion beam lithography, X-ray lithography, or any other radiation method in a preferred embodiment, the radiation is UV, near IR, or visible light. The light source may be coherent or noncoherent. The protective group may alternatively be an electrochemically-sensitive group which may be removed in the presence of an electric current.

In some embodiments, the exposed area is less than about 1 cm$^2$ or less than about 1 mm$^2$. In preferred embodiments the exposed area is less than about 10,000 μm$^2$ or, more preferably, less than about 100 μm$^2$. Spaces between activated regions are not critical and will generally be greater than about 1 μm.

When photoactivatable binding members are used, they are preferably exposed to light through a suitable mask using photolithographic techniques well known in the semiconductor industry and described in, for example, Sze, *VLSI Technology,* McGraw-Hill (1983), which is incorporated herein by reference. In one embodiment, the mask is a transparent support material coated with a layer of opaque material. Portions of the opaque material are removed, leaving opaque material in the precise pattern desired on the substrate surface. The mask is brought into close proximity with or directly into contact with the surface. Openings in the mask correspond to locations on the surface where it is desired to photoremove protecting groups from the binding members. Alignment may be performed using conventional alignment techniques in which alignment marks are used to accurately overlay successive masks with previous patterning steps. Other alignment techniques may be used, for example, interferometric techniques such as the one described in Flanders, et al., "A New Interferometric Alignment Technique," *App. Phys. Lett.* (1977) 31:426–428, which is incorporated herein by reference.

To enhance contrast of light applied to the substrate it may be desirable to provide contrast enhancement materials between the mask and the substrate. This contrast enhancement layer may comprise a molecule which is decomposed by light such as quinone diazide.

The light may be from a conventional incandescent source, an arc lamp, a laser, or the like. If noncoherent sources of light are used it may be desirable to provide a thick- or multi-layered mask to prevent spreading of the light on the substrate. Generally, lasers may be preferable because they can more easily provide wavelengths particularly suited for a chromophore of the photosensitive group.

While the invention is illustrated primarily herein by way of the use of a mask to illuminate the substrate, other techniques may also be used. For example, the substrate may be rotated under a modulated laser or diode light source. Such techniques are discussed in, for example, U.S. Pat. No. 4,719,615, which is incorporated herein by reference.

The substrate may be irradiated either in contact with or not in contact with a solution and, preferably, is irradiated in contact with the solution. The solution may contain reagents to prevent by-products of irradiation from interfering with subsequent binding reactions. Such by-products might include, for example, carbon dioxide, nitrosocarbonyl compounds, styrene derivatives, indole derivatives, and products of their photochemical reactions. Reagents added to the solution may include, for example, acidic or basic buffers, thiols, substituted hydrazines and hydroxylamines, reducing agents (e.g., NADH or bisulfite ion) or reagents known to react with a given functional group (e.g., aryl nitroso+glyoxylic acid→aryl formhydroxamate+$CO_2$). Preferably, however, protecting groups will be selected which do not cause significant interferences with the binding reactions. Also, wash steps will be incorporated so that the by-products do not interfere with the reactions.

In a preferred embodiment, a surface provided with a plurality of sites occupied by photosensitive N-derivatives of biotin or biotin analogs is exposed to a desired light pattern to cause loss of some or all of the photosensitive protecting groups at predefined regions on the surface. Such irradiation of the N-derivatized biotin compounds of the present invention leads to formation of surface-bound biotin or biotin analogs having a strong specific binding affinity for avidin or avidin analogs. The specific binding affinity of biotin and avidin is one of the strongest known between macromolecules ($K_a = 10^{15}$ $M^{-1}$). This binding persists when the carboxyl terminus of biotin is attached to another entity, e.g., a surface, or when avidin is attached to another molecule. Avidin possesses four subunits having specific binding affinity for biotin molecules. For example, deprotected biotin sites may be incubated with avidin or an avidin conjugate of an anti-ligand, e.g., an antibody, to provide a localized concentration of the desired anti-ligand on the surface. When incubation with avidin alone is performed, it is necessary to further incubate the resulting product with a preselected species having specific binding affinity for avidin, e.g., a biotinylated anti-ligand. Thus, biotinylated anti-ligands can be bound to the free sites of avidin to afford anti-ligands immobilized at predefined regions on the surface. For a general discussion of the use of the biotin-avidin interaction in molecular biology, see Bayer, et al. Once localization of the anti-ligand is complete, the light pattern can be changed and the same or a different anti-ligand can be localized at other discrete sites on the surface.

V. Attachment of Anti-ligands

An anti-ligand is one or more molecules that recognize a particular ligand in solution. Examples of ligands that can be investigated by this invention include, but are not restricted to agonists and antagonists for cell membrane receptors, toxins and venoms, viral epitopes, antigenic determinants, hormones, hormone receptors, steroids, peptides, enzymes, substrates, cofactors, drugs, lectins, sugars, oligonucleotides, oligosaccharides, proteins, and monoclonal and polyclonal antibodies.

Anti-ligands that mediate a biological function on binding with particular ligand(s) are of most interest. Suitable anti-ligands include relatively small, single molecules, such as cofactors, which show specific binding properties. Typically, anti-ligands will be greater than about 100 daltons in size and more typically will be greater than about 1 kD in size. Other examples of antiligands include, but are not restricted to, the common class of receptors associated with the surface membrane of cells and include, for instance, the immunologically important receptors of B-cells, T-cells, macrophages and the like. Other examples of anti-ligands that can be investigated by this invention include but are not restricted to hormone receptors, hormones, drugs, cellular receptors, membrane transport proteins, steroids, peptides, enzymes, substrates, cofactors, vitamins, lectins, sugars, oligonucleotides, oligosaccharides, viral epitopes, antigenic determinants, glycoproteins, and immunoglobulins, e.g., monoclonal and polyclonal antibodies.

In a preferred embodiment, the anti-ligand will be a biotinylated receptor which binds specifically to avidin. Many biotinylated anti-ligands and biotinylating reagents are commercially available. (See, for example, *Vector Laboratories, Inc., Catalog,* Burlingame, Calif.) Methods for biotinylating desired anti-ligands are wellknown in the art and are described, for example, in Bayer, et al.

In a preferred embodiment a plurality of anti-ligands is immobilized on a surface by first attaching photoreactive caged binding members to the surface. The caged binding members on a predefined region of the surface are exposed to light to give binding members having a high affinity for a specific binding substance. The activated binding members on the predefined region are then incubated with the specific binding substance, the surface is washed free of unbound specific binding substance, and the surface is incubated with a desired antiligand or anti-ligand conjugate. The exact incubation conditions, e.g., time, temperature, pH, will depend upon the species used and will be readily apparent to one skilled in the art. After washing the surface free of unbound anti-ligand, the above steps can be repeated on a different region of the surface.

In another embodiment of the invention a plurality of anti-ligands is immobilized on a surface as described above, except the attachment of anti-ligands to specific binding substance is carried out prior to introducing the specific binding substance to the surface.

In a further embodiment the anti-ligand is a monoclonal or polyclonal antibody. In a still further preferred embodiment the anti-ligand is a biotinylated antibody or biotinylated receptor.

A most preferred embodiment of the invention is when the binding member is biotin or a biotin analog and the specific binding substance is avidin or an avidin analog.

VI. Screenings and Assays

A surface prepared according to the methods described above can be used to screen for ligands having high affinity for immobilized anti-ligands. Screening can be performed by immobilizing a plurality of anti-ligands on predefined regions of a surface by the methods described above. A solution containing a marked (labelled) ligand is introduced to the surface and incubated for a suitable period of time. The surface is then washed free of unbound ligand and the anti-ligands having high affinity for the ligand are identified by identifying those regions on the surface where markers are located. Suitable markers include, but are not limited to, radiolabels, chromophores, fluorophores, chemiluminescent moieties, and transition metals. Alternatively, the presence of ligands may be detected using a variety of other techniques, such as an assay with a labelled enzyme, antibody, and the like. Other techniques using various marker systems for detecting bound ligand will be readily apparent to those skilled in the art.

In a preferred embodiment, a substrate prepared as discussed above can be exposed to a solution containing a marked ligand such as a marked antigen. The ligand can be marked in any of a variety of ways, but in one embodiment marking is effected with a radioactive label. The marked antigen binds with high affinity to an immobilized antibody previously localized on the surface. After washing the surface free of unbound ligand, the surface is placed proximate to x-ray film to identify the antibodies that recognize the antigen. Alternatively, a fluorescent marker may be provided and detection may be by way of a charge-coupled device (CCD), fluorescence microscopy or laser scanning.

When autoradiography is the detection method used, the marker is a radioactive label, such as $^{32}p$. The marker on the surface is exposed to X-ray film, which is developed and read out on a scanner. An exposure time of about 1 hour is typical in one embodiment. Fluorescence detection using a fluorophore label, such as fluorescein, attached to the ligand will usually require shorter exposure times.

Quantitative assays for ligand concentrations can also be performed according to the present invention. In a direct assay method, the surface containing localized anti-ligands prepared as described above, is incubated with a solution containing a marked ligand for a suitable period of time. The surface is then washed free of unbound ligand. The amount of marker present at predefined regions of the surface is then measured and can be related to the amount of ligand in solution. Methods and conditions for performing such assays are well-known and are presented at, for example, L. Hood, et al., *Immunology*, Benjamin/Cummings (1978) and E. Harlow, et al., *Antibodies. A Laboratory Manual*, Cold Spring Harbor Laboratory, (1988). See, also U.S. Pat. No. 4,376,110 for methods of performing sandwich assays. The precise conditions for performing these steps will be apparent to one skilled in the art.

A competitive assay method can also be employed by the present invention. Such a method involves immobilizing anti-ligands on predefined regions of a surface as described above. An unmarked ligand is then bound to anti-ligands on the surface having specific binding affinity for the ligand. A solution containing marked ligand is then introduced to the surface and incubated for a suitable time. The surface is then washed free of unbound reagents and the amount of marker remaining on the surface is measured. Alternatively, marked and unmarked ligand can be exposed to the surface simultaneously. The amount of marker remaining on predefined regions of the surface can be related to the amount of unknown ligand in solution.

Use of the invention herein is illustrated primarily with reference to screenings of ligands for anti-ligands and assays for ligands. The invention will, however, find many other uses. For example, the invention may be used in information storage (e.g., on optical disks), production of molecular electronic devices, production of stationary phases in separation sciences, and in immobilization of cells, proteins, lectins, nucleic acids, polysaccharides and the like in any desired pattern on a surface via molecular recognition of a specific anti-ligand.

The invention has been described primarily with reference to the use of photoremovable protecting groups, but it will be readily recognized by those of skill in the art that other types of groups can be used and that other sources of radiation can also be used. For example, in some embodiments it may be desirable to use protecting groups sensitive to electron beam irradiation, X-ray irradiation, X-ray lithography, or combinations thereof. Alternatively, the group could be removed by exposure to an electric current.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

VII. Examples

The following examples of preferred embodiments of the present invention are presented by way of illustration only and do not suggest that the above- described methods and compositions are in any way limited by the specific examples set forth below.

Synthesis of Photoreactive N-1'-Derivatives of Biotin

Methods for the preparation of acyl imidazolidones, such as biotin derivatives, are well-known. See, for example, Kohn, et al., *J. Org. Chem.* (1977), 42, 941–948 and Knappe, et al., Biochem. Z. (1961), 235, 168–176. Treatment of biotin methyl ester with methyl chloroformate in refluxing chloroform (no base) for 72–80 h afforded a mixture heavily favoring the N-1'-derivative. Under similar conditions, the use of nitroveratryloxycarbonyl (NVOC) chloride (Amit, et al., *J. Org. Chem.* (1974), 39, 192–196) gave N-1'-(nitroveratryloxycarbonyl)-biotin methyl ester (NVOC-biotin-OMe) in 47% yield after chromatography and crystallization. Likewise, N-1'-(nitroveratryloxycarbonyl)-biotin p-nitrophenyl ester (NVOC-biotin-ONP) was obtained in 39% yield.

The structural assignment is based on precedent as well as spectroscopic properties. See, for example, E. Becker, *High Resolution NMR*, 2nd ed., Acad. Press (1980). In particular, the 1H NMR spectrum readily differentiates the ring fusion protons bearing 1) a urea nitrogen (ca 4.2 ppm) and 2) an imide nitrogen (ca 4.8 ppm). Through the use of COSY (Derome, *Modern NMR Techniques for Chemistry Research*, Pergamon Press, Oxford (1987)) on N-1'-(nitroveratryloxycarbonyl)-biotin p-nitrophenyl ester, it was determined that the former ring fusion proton is vicinal to a methine adjacent to sulfur, and that the latter is vicinal to a methylene adjacent to sulfur.

Using the conditions reported by Kohn, etal. biotin methyl ester is similarly derivatized with dimethyldimethoxycarbobenzyloxycarbonyl (DDZ) chloride or 1-pyrenylmethyloxycarbonyl (PYROC) chloride to afford the photolabile compounds N-1'-(dimethyldimethoxycarbobenzyloxycarbonyl) biotin methyl ester (DDZ-biotin-OMe) and N-1'-(1-pyrenylmethyloxycarbonyl) biotin methyl ester (PYROL-biotin-OMe), respectively. The methods of Knappe, et al., and Kohn, et al., can be employed to prepare analogous compounds and are incorporated by reference herein.

EXAMPLE A

Preparation of NVOC-biotin-OMe
(N-1'-(6-nitroveratryloxycarbonyl)-biotin methyl ester)

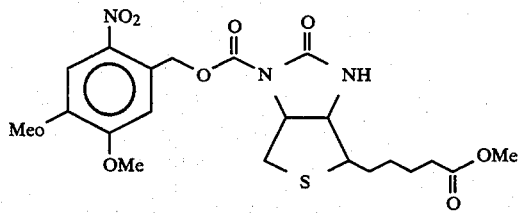

2.00 g (8.19 mmol) of D-biotin was added to a methanolic HCl solution prepared from 2.5 ml of acetyl chloride in 40 ml of anhydrous methanol. After stirring for 15 hours, the solvent was removed under reduced pressure to afford 2.11 g of the product biotin-OMe (biotin methyl ester) as a white solid, MP 116°–118° C. (100% yield).

NVOC-biotin-OMe was prepared from biotin via the intermediate, biotin methyl ester (biotin-OMe) by either of two methods.

1. A solution of 1.00 g (3.87 mmol) of biotin-OMe and 1.60 g (5.81 mmol) of 6-nitroveratryloxycarbonyl chloride in 10 ml of chloroform was heated to reflux for 50 hours. The product was purified via flash-column chromatography on silica gel (3% methanol, 3% acetone, 94% chloroform as eluent) to afford 0.90 g of NVOC-biotin-OMe as a yellow solid (47% yield, 84% yield based on unreacted starting biotin-OMe), MP 199°–203° C., and 0.44 g of recovered biotin-OMe (44% recovery). The product, NVOC-biotin-OMe, was recrystallized from methylene chloride/ether.

2. A solution of 3.4 g (12 mmol) of 6-nitroveratryloxycarbonyl chloride in 40 ml of methylene chloride was added to a solution of 1.1 ml (14 mmol) of pyridine and 1.3 g (13 mmol) of phenol in 15 ml of methylene chloride cooled to 0° C. The reaction mixture was allowed to warm to room temperature and was stirred for 19 hours. The solution was partitioned between methylene chloride and 1N HCl, the organic phase was separated and dried with magnesium sulfate, and the solvent was removed under reduced pressure to give 4.1 g of a brown oil. Purification via flash-column chromatography on silica gel (90% methylene chloride/10% hexane as the eluent) afforded 2.0 g of the product, 6-nitroveratryl phenyl carbonate, as a colorless oil.

A mixture of 399 mg (1.20 mmol) of 6-nitroveratryl phenyl carbonate in 5 ml of chloroform and 202 mg (0.782 mmol) of biotin-OMe were heated to reflux. After 50 hours TLC showed that no reaction occurred, therefore 35 mg of 60% sodium hydride (0.88 mmol) was added in two equal portions over 15 minutes. After an additional 16 hours at reflux, the reaction was quenched with 3 drops of glacial acetic acid. The product was purified via flash-column chromatography on silica gel (3% methanol, 3% acetone, 94% chloroform as the eluent) to afford 264 mg of the product, NVOC-biotin-OMe, as an off-white solid (68% yield, 75% yield based on recovered unreacted biotin-OMe) and 20 mg of recovered biotin-OMe (10% yield).

EXAMPLE B

Preparation of NVOC-biotin-ONP
(N-1'-(6-nitroveratryloxycarbonyl)-biotin
para-nitrophenyl ester)

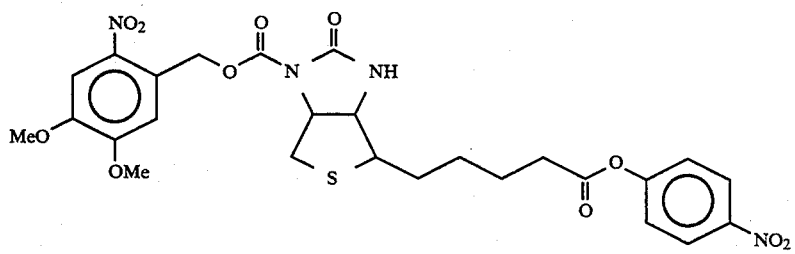

A mixture of 0.340 g (0.930 mmol) of biotin p-nitrophenyl ester (purchased from Sigma Chemical Co., St. Louis) and 0.450 g (1.63 mmol) of 6-nitroveratryloxycarbonyl chloride in 4 ml of chloroform was heated to reflux for 65 hours. The mixture was purified via flash-column chromatography on silica gel (3% methanol, 3% acetone, 94% chloroform as the eluent) to produce 0.231 g of NVOC-biotin-ONP as a beige solid (39% yield, 93% yield based on unreacted biotin-ONP), MP 203°–205° C., and 0.21 g of recovered unreacted biotin-ONP (58% yield). The product was further purified via recrystallization from chloroform/hexane.

EXAMPLE C

Preparation of NPOC-biotin-ONP
(N-1'-(6-nitropiperonyloxycarbonyl)-biotin
paranitrophenyl ester)

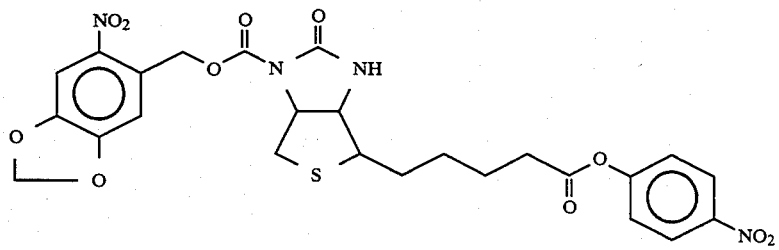

A mixture of 0.365 g (1.00 mmol) of biotin p-nitrophenyl ester and 0.410 g (1.58 mmol) of 6-nitropiperonyloxycarbonyl chloride in 5 ml of chloroform was heated at reflux for 62 hours. The product was purified via flash-column chromatography on silica gel (3% methanol, 3% acetone, 94% chloroform as the eluent) to produce 0.231 g of product as a beige solid (39% yield, 93% based on unrecovered starting material), MP 203°–205° C., and 0.21 g of recovered biotin-ONP (58% yield). As described, the product was further purified via recrystallization from chloroform/hexane.

EXAMPLE D

Preparation of NVOC-DT-biotin-OMe
(N-1'-(6-nitroveratryloxycarbonyl)-dethiobiotin methyl ester)

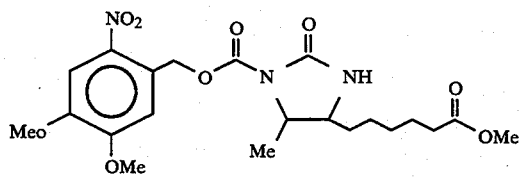

A slurry of 50 mg (0.19 mmol) of biotin-OMe and about 1 g of Raney Nickel active catalyst (50% solution in H2O from Aldrich Chemical Co.) in 4 ml of methanol was stirred at room temperature for one hour. The reaction mixture was diluted with chloroform, filtered and the recovered catalyst was washed with methanol. The combined wash and filtrate were partitioned between chloroform and saturated sodium chloride acidified to pH 2 with 1N HCl. The combined organic phases were dried over magnesium sulfate, and the solvent removed under reduced pressure to give 34 mg of pure DT-biotin-OMe as a white solid, MP 68°–72° C. (77% yield).

A mixture of 34 mg (0.15 mmol) of DT-biotin methyl ester and 74 mg (0.27 mmol) of 6-nitroveratryloxycarbonyl chloride in 3 ml of chloroform was heated to reflux for 15 hours. The products are purified via flash-column chromatography on silica gel (3% methanol, 97% chloroform as the eluent) to afford 45 mg of a 1:3 mixture of products as a yellow solid (65% yield), MP 152°–156° C.

EXAMPLE E

Preparation of NVOC-biotin-OH
(N-1'-(6-nitroveratryloxycarbonyl)-biotin)

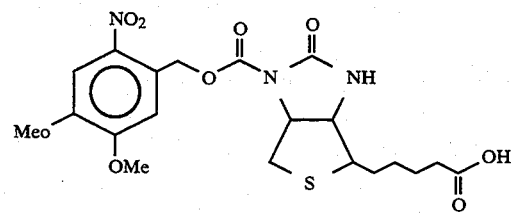

A solution of 262 mg (0.527 mmol) of NVOC-biotin-OME, prepared in by either method of Example A, in 15 ml of tetrahydrofuran and 2 ml of dimethylforamide was treated with 10 ml of 1N HCl. The reaction mixture was heated to reflux for 49 hours, cooled to room temperature, and the solvent removed under reduced pressure. The crude product was purified via flash-column chromatography on silica gel (10% methanol, chloroform as the eluent) to afford 178 mg of the pure product, NVOC-biotin-OH, as a white solid (70% yield), MP 219°–223° C.

EXAMPLE F

Chromatographic Evidence for Photoremoval of the NVOC group from NVOC-biotin-ONP A 100 mM solution of NVOC-biotin-ONP in acetonitrile, or biotin in water, was placed in a quartz cuvette with a 2.0 mm pathlength. The cuvette was irradiated for two minutes at a power of 1 watt/cm$^2$ with a 500 W Hg(Xe) arc lamp (Oriel #66142) having a 305 nm long pass filter (Oriel #51450). Illuminated and non-illuminated samples were then subjected to reverse-phase HPLC.

Shown in FIG. 1 are chromatographs of illuminated biotin and illuminated NVOC-biotin-ONP. The results support the following: 1) biotin was unaffected by the illumination; and 2) NVOC-biotin-ONP was converted to Biotin-ONP by the illumination.

EXAMPLE G

Estimation of the Affinity of NVOC-biotin-OMe for Avidin Before and After Illumination All procedures using NVOC-biotin-OMe were conducted in dim red light. NVOC-biotin-OMe was dissolved in dimethylformamide (DMF) to a concentration 1 mM and diluted to 100 μM with phosphate-buffered saline pH 7.4. In order to remove any contaminants having high affinity for avidin, 2 ml of the NVOC-biotin-OMe solution was mixed with 1 ml of packed streptavidin-Sepharose-4B resin (SIGMA) which had been washed thoroughly to remove any non-covalently bound avidin. After stirring for three hours, the resin was removed by centrifugation followed by filtration (0.2 micron nylon filter). The concentration of the NVOC-biotin-OMe solution (measured by 350 nm absorbance) was not significantly reduced by the resin treatment.

Microtiter wells (Beckman EIA plates) were treated for 1 hr with 200 μl of 0.5 μg/ml of streptavidin in 10 mM sodium bicarbonate buffer (pH 9.6). After removal of the streptavidin solution and washing with phosphate buffered saline (PBS)/0.05% Tween 20, the wells were incubated for 1 hr at room temperature with 200 μl of PBS containing various concentrations of illuminated (as detailed above) and non-illuminated biotin or streptavidin-Sepharose treated NVOC-biotin-OMe. The wells were then washed with PBS/Tween 20 and incubated for 1 hr at room temperature with 200 μl of PBS containing $^3$H-biotin (30 Ci/mmol, New England Nuclear). The wells were then washed with PBS/Tween and treated for 30 minutes at room temperature with 200 μl of 10% trichloroacetic acid in water. The radioactivity in 100 μl was then determined by liquid scintillation counting.

The results of a representative binding experiment are shown in FIG. 2. The experiment was done three times with similar results. The data indicate that NVOC-biotin-OMe has very low affinity for avidin as indicated by the fact that pre-incubation of avidin with concentrations of NVOC-biotin-OMe ("caged biotin") as high as $10^{-5}$M had no significant effect on the subsequent binding of $^3$H-biotin. In addition, the results indicate that illumination of NVOC-biotin-OMe generates a biotin derivative ("IL caged biotin") that was nearly as effective as biotin in blocking the subsequent binding of 3H-biotin. Combined with the chromatographic evidence above, the data indicate that illumination of NVOC derivatives of biotin leads to removal of the NVOC group.

EXAMPLE H

Demonstration of Photoremoval of NVOC group from NVOC-Biotin Attached to a Membrane Nitrocellulose membrane filters (Biorad) were reacted with 5% bovine serum albumin in Tris-buffered saline (TBS) for 3 hr at room temperature. The membranes were washed with TBS, cut into 1 cm$^2$ sections and then reacted for 3 hr at room temperature (in the dark) with 10% DMSO/100 mM sodium borate buffer (pH 8.6) alone, 10 mM of biotin-N-hydroxysuccinimidyl ester in 10% DMSO/100 mM sodium borate buffer (pH 8.6), or NVOC-biotin-ONP in 50% DMSO/100 mM sodium borate buffer (pH 8.6). After washing with TBS, half the sections that were treated with NVOC-biotin-ONP were illuminated in a manner identical to that described above. After washing with TBS, the membrane sections were incubated for 1 hr at room temperature with TBS containing 0.1% bovine serum albumin and 0.1 µCi/ml $^{125}$I-streptavidin (Amersham). After washing with TBS, radioactivity on the membrane section was quantitated by gamma counting.

FIG. 3 shows the data for a representative experiment. Binding of $^{125}$I-streptavidin was approximately 3-fold higher with biotinylated membranes than with control membranes. Binding of $^{125}$I-streptavidin to non-illuminated NVOC-biotinylated membranes was not significantly different from non-biotinylated control membranes. $^{125}$I-streptavidin binding to illuminated NVOC-biotinylated membranes was approximately equal to that of biotinylated membranes. These data indicate that membrane-bound NVOC-biotin has low affinity for streptavidin and that illumination greatly increases streptavidin binding by removing the NVOC group from the biotin group.

Immobilization of anti-ligands on solid supports

EXAMPLE I

Preparation of Caged-Biotin Glass Plates

Commercially available glass microscope slides were derivatized with N-BOC-aminopropyltriethoxy silane according to literature procedures (for example, see J. Chromatography, 1974, Vol. 97, p. 33). The slides were incubated in a solution of 20% trifluoroacetic acid in methylene chloride for 30 minutes to remove the BOC protecting group. After washing sequentially with methylene chloride, dimethylformamide, and ethanol, the slides were neutralized by immersing in a solution of 10% diisopropylethyl amine in methylene chloride for 30 minutes and further washed with methylene chloride.

N-BOC-6-aminocaproic acid was converted to the BOP-activated ester in preparation for reaction with the derivatized glass slide. A solution of a 197 mg (0.445 mmol) of benzotriazol-1-yloxy-tris(dimethylamino)-phosphonium hexafluorophosphate (BOP) in 0.40 ml of dimethylformamide was added to a solution of 86 mg (0.37 mmol) of N-BOC-6-aminocaproic acid, 56 mg (0.4 mmol) of 1-hydroxybenzotriazole hydrate (HOBT), and 0.14 ml (0.80 mmol) of diisopropylethyl amine in 0.40 ml of dimethylformamide. After 10 minutes the resultant solution was diluted with 3.20 ml of dimethylformamide to give a 0.10M solution of the activated ester.

The derivatized slides were incubated with 0.5 ml of the activated ester solution and after two hours of coupling, were sequentially washed with dimethylformamide, ethanol and methylene chloride. The BOC protecting groups were removed from the aminocaproic acid moieties, and the slide was subsequentially washed as described above. Biotin derivatives were coupled to the glass plates by either of two methods, as illustrated for NVOC-biotin.

Method A (via the BOP ester)

The BOP derivative of NVOC-biotin-OH was prepared by adding a solution of 40 mg (0.099 mmol) of BOP in 0.09 ml of dimethylsulfoxide to a solution of 43 mg (0.090 mmol) of NVOC-biotin-OH, 13 mg (0.096 mmol) of HOBT, and 0.035 ml of diisopropylethyl amine in 0.090 ml of dimethylsulfoxide. After five minutes, the resulting solid was diluted to 1.80 ml with dimethylsulfoxide to give a 0.05M solution of the activated ester. Approximately 0.5 ml of the activated ester solution was applied to the surface of the derivatized glass surface. After being exposed to the activated ester for two hours, the slides were washed sequentially with dimethylformamide, ethanol, and methylene chloride to yield a NVOC-biotin-caproic-propyl derivatized surface.

Method B (via the ONP ester)

Approximately 0.5 ml of an 0.10M solution of NVOC-biotin-ONP in dimethylformamide was applied to the surface of the derivatized glass slide. After 2–24 hours, the slides were washed sequentially with dimethylformamide, ethanol, and methylene chloride to yield a NVOC-biotin-caproic-propyl derivatized surface.

EXAMPLE J

Photodeprotection of an NVOC-Biotin-Caproic-Propyl-derivatized slide, and subsequent labeling with a Fluorescein-Streptavidin conjugate A glass microscope slide to which NVOC-biotin has been covalently attached via a caproic-propyl spacer, as described in the Example I, was mounted on a custom flow cell and illuminated through a 500 µm×500 µm checkerboard-pattern mask (Photo Sciences Inc., Torrance, Calif.) using broad-band UV/blue light. The light source was a 500 W Mercury arc lamp (Oriel Model 87330) equipped with a 350 nm–450 nm dichroic reflector and produced actinic light having an intensity of 12 mW/cm$^2$ as measured through a 360 nm bandpass filter. The derivatized surface was photolyzed in flowing dioxane for 15 minutes, removed from the flow cell, and sequentially rinsed in deionized water, ethanol, and methylene chloride.

After incubation for one hour in a solution containing filtered PBS, 1% BSA, 0.05% Tween 20, pH 7.4, the activated surface was treated with a solution containing a Fluorescein-derivative of Streptavidin (Molecular Probes; 10 µg/ml in PBS/BSA/Tween 20) for one hour at room temperature. The slide was vortexed twice in PBS, 0.05% Tween 20, pH 7.4 for 10 minutes, rinsed with deionized water, and allowed to dry. The slide was examined with a scanning fluorescence microscope (Zeiss Axioskop equipped with a Newport Model PM500-C motion controller, a Spectra-Physics Model 2020 -argon-ion laser producing a 488 nm excitation light; and a 520 nm long-pass emission filter) interfaced with a photon-counting device (Hamamatsu Model 9403-02 photomultiplier; Stanford Research Systems Model SR445 amplifier and Model SR430 multichannel scaler, IBM compatible FC) to generate a two-dimensional image consisting of fluorescence intensity data as a function of x,y position. An example of this technique is described in U.S. Pat. No. 5,143,854, which is a continuation-in-part of now abandoned U.S. Ser. No. 362,901, filed Jun. 7, 1989; the patent and application are incorporated herein by reference. FIG. 4 shows an example of the images obtained.

The light squares indicate regions of high fluorescence intensity resulting from localization of the fluorescein label attached to the anti-ligand- This experiment demonstrates enhanced binding of streptavidin upon photodeprotection of NVOC-biotin coupled to a surface with a caproic-propyl spacer, and spatially-addressable immobilization of an anti-ligand, such as streptavidin, by non-covalent means.

EXAMPLE K

Figure 5:
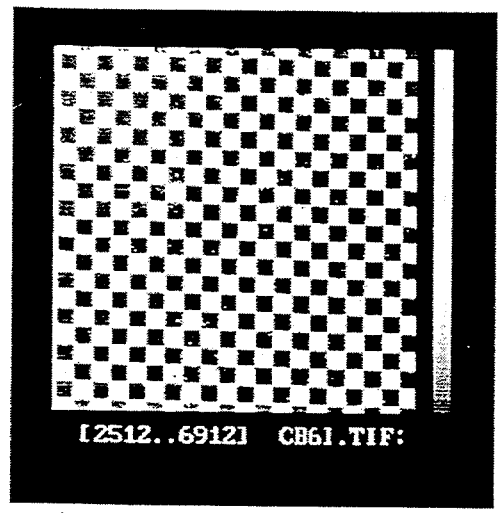
FIG. 5 presents fluorescence results showing the spatial immobilization of Fluorescein-Biotin on a surface modified with Streptavidin.

Photodeprotection of an NVOC-Biotin-Caproic-Propyl-derivatized slide, treatment with Streptavidin, and labeling with a Fluorescein-Biotin conjugate The microscope slide of Example I having NVOC-biotin covalently attached via a caproic-propyl spacer was illuminated and processed as in Example J, except that after preincubation with the PBS/BSA/Tween 20 solution, the surface was treated with 10 μg/ml solution of Streptavidin (in pBS/BSA/Tween 20) for 40 minutes at room temperature, followed by incubation with a 1 μM solution of Fluorescein-Biotin (5-(N-((5-(N-(6-(biotinoyl)amino) hexanoyl)amino)pentyl)thioureidyl)-fluorescein, in PBS, pH 7.4) for 20 minutes. The resulting slide was then washed, dried, and examined using a scanning fluorescence microscope as described above. FIG. 5 shows an example of the images obtained.

The light squares indicate regions of high fluorescence intensity resulting from localization of the fluorescein label attached to ligand, biotin. This experiment demonstrates the binding of a ligand (a Fluorescein-Biotin complex) to streptavidin immobilized in a spatially-addressable manner.

EXAMPLE L

Figure 6:
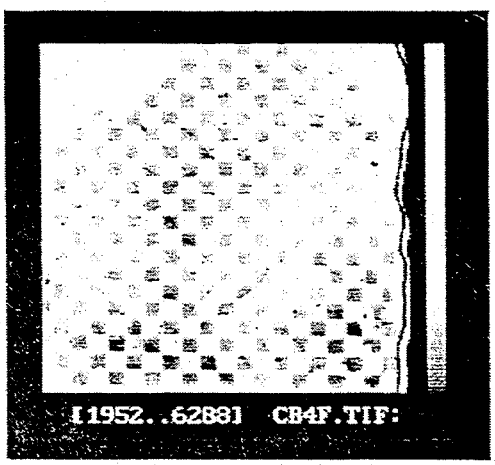
FIG. 6 presents fluorescence results showing the spatial immobilization of Fluorescein-Streptavidin on a surface having biotin bound by a polyether linker.

Photodeprotection of an NVOC-Biotin-Polyether-derivatized slide and labeling with a Fluorescein-Streptavidin conjugate A microscope slide to which 3-aminopropyltriethoxy silane had been attached was treated with the BOP-activated ester of 18-amino-6-aza-10,15-dioxa-5-ketooctadecanoic acid using a procedure similar to Example I. The resulting slide was then derivatized with NVOC-Biotin-ONP, and was illuminated, processed, and examined as described in Example J. FIG. 6 shows an example of the images obtained.

This experiment demonstrates spatially-localized streptavidin binding upon photodeprotection of NVOC-Biotin coupled to a surface using an alternative linker, a polyetherglutaric-propyl moiety.

EXAMPLE M

Figure 7:
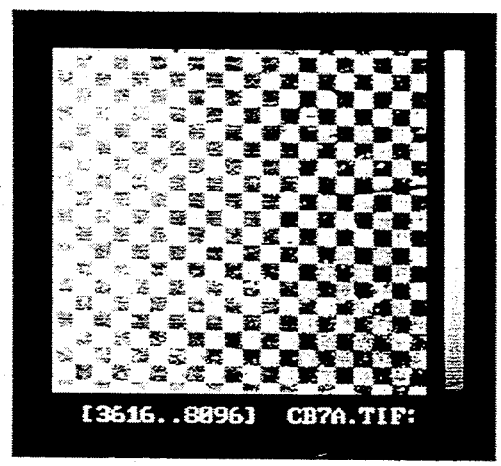
FIG. 7 presents fluorescence results showing the spatial immobilization of Fluorescein-Streptavidin on a biotinylated surface.

Photodeprotection of an NPOC-Biotin-Caproic-Propyl-derivatized slide and labeling with a Fluorescein-Streptavidin conjugate The microscope slide to which NPOC-biotin-ONP had been covalently attached via a caproic-propyl spacer was illuminated, processed, and examined as described in Example J. FIG. 7 shows an example of the images obtained.

This experiment demonstrates spatially-localized streptavidin binding upon photodeprotection of caged-biotin using a different protecting group, NPOC.

EXAMPLE N

Figure 8:
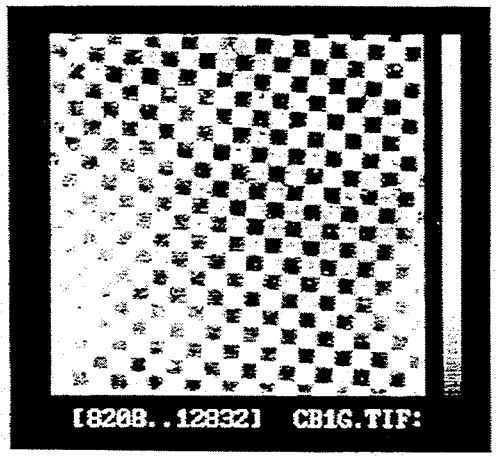
FIG. 8 presents fluorescence results showing the spatial immobilization of Bodipy-Streptavidin on a biotinylated surface.

Photodeprotection of an NVOC-Biotin-Caproic-Propyl-derivatized slide in aqueous buffer and labeling with a Bodipy-streptavidin conjugate The microscope slide of Example I having NVOC-Biotin covalently attached via a caproic-propyl spacer was mounted on a custom flow cell and illuminated using the apparatus described in Example J. The derivatized surface was photolyzed in PBS, 1% BSA, 0.1% Tween 20 for 30 minutes at 12 mW/cm$^2$, removed from the flow cell, and processed as described in Example K, except that Bodipy-streptavidin (Molecular Probes, 50 μg/ml) was used instead of the fluorescein conjugate. FIG. 8 shows an example of the images obtained.

This experiment demonstrates spatially-localized streptavidin binding upon photodeprotection of NVOC-biotin in a different solvent, in this case an aqueous buffer.

EXAMPLE O

Evaluation of crosslinking groups of different lengths

Figure 9:
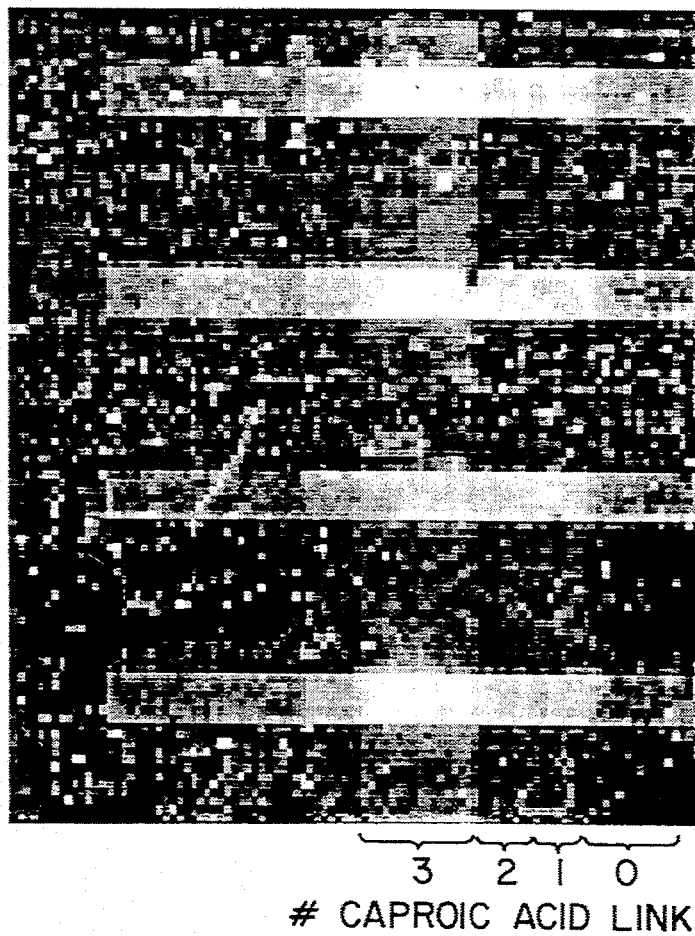
FIG. 9 presents fluorescence results showing the effect of inserting linkers of different lengths on the binding of Fluorescein-Streptavidin.

A microscope slide derivatized with N-Boc-3-aminopropyltriethoxy silane, as in Example I, was functionalized with three different crosslinkers in different locations by selectively coupling 1, 2 or 3 N-Boc-6-aminocaproic acid linkers to the surface via their BOP-activated esters. This generated four distinct and well defined regions on the surface of the slide having zero, one, two and three 6-aminocaproic acid linkers (4, 11, 18 and 25 atom spacers, respectively) between the surface and the terminal amino functionality used to bind to the carboxyl group of the derivatized biotin. A 0.1M solution of biotin p-nitrophenyl ester in dimethylformamide was subsequently coupled to the slide, and the relative binding affinity of streptavidin to the surface-bound biotin was measured by incubating the slide with fluoresceinated streptavidin and measuring the fluorescence intensity as in Example J. The measured relative fluorescence was 38, 68, 85 and 100% (normalized to the fluorescence of area having three caproic linkers), respectively, for zero, one two and three caproic linkers, showing that a higher density of streptavidin was bound to an area of the slide derivatized with biotin spaced relatively far from the surface of the slide. FIG. 9 shows the fluorescence of fluoresceinated streptavidin bound to the glass slide derivatized in this experiment.

EXAMPLE P

Photodeprotection of an NVOC-Biotin-Caproic-Propyl-derivatized slide and subsequent immobilization of antibodies on the derivatized surface.

A microscope slide to which NVOC-Biotin had been covalently attached via a caproic-propyl spacer was mounted on a custom flow cell and illuminated as described in Example J, except that a hand-cut mask consisting of a horizontal stripe (approximately 2 mm wide) was used. After removal from the flow cell and rinsing, the slide was incubated for 30 minutes with PBS, 1%

BSA, 0.05% Tween 20, pH 7.4, followed by 30 minutes treatment with Streptavidin (10 μg/ml in PBS/BSA/-Tween 20), rinsing with PBS, 0.05% Tween 20, 60 minutes incubation with biotinylated Rabbit IgG (Vector Laboratories; 50 μg/ml in PBS/BSA/Tween 20), and rinsing with PBS/Tween 20. The surface was then "capped" to prevent subsequent streptavidin binding to the multiple biotin moieties on the biotinylated IgG. That is, streptavidin was used to bind free biotin on IgG. This was accomplished by re-treatment with Streptavidin solution, rinsing with PBS/Tween 20, followed by incubation with free biotin (Molecular Probes; 1 mM in PBS/Tween 20; 10 minutes), and a final PBS/Tween 20 rinse. The slide was then re-mounted on the flow cell, photolyzed for 30 minutes in PBS/Tween 20 using a hand-cut mask consisting of vertical stripes (approximately 2 mm wide), and processed as described above, except that biotinylated Mouse IgG (Vector Laboratories; 50 μg/ml in PBS/BSA/Tween 20; 30 minute incubation) was used, and the "capping" steps were not repeated. The slide was then rinsed with deionized water, allowed to dry, and beads of silicone gasket compound (Permatex Ultra Blue) were used to partition the slide into three areas. After pre-incubation for 30 minutes with PBS/BSA/-Tween 20, the first area was treated with Fluorescein-labeled anti-Rabbit IgG (Vector Laboratories; made in goat; 100 μg/ml in PBS/BSA/Tween 20). The second area was treated with Fluorescein-labeled anti-Mouse IgG (Vector Laboratories; made in horse; 100 μg/ml in PBS/BSA/Tween 20). The third area was incubated with an equimolar mixture of the two secondary antibodies. The slide was then vortexed twice in PBS/Tween 20 for two minutes, rinsed briefly with deionized water, and allowed to dry. The different regions of the slide were examined using the scanning fluorescence microscope described in Example J.

Figure 10A:
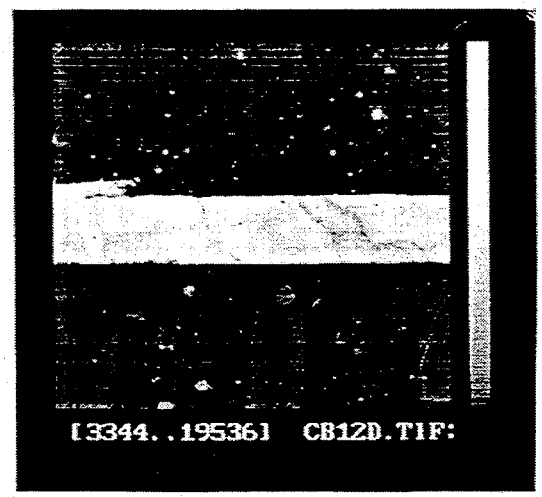
FIG. 10a presents fluorescence results showing binding of Fluorescein-anti-Rabbit IgG to a slide having multiple anti-ligands.
Figure 10B:
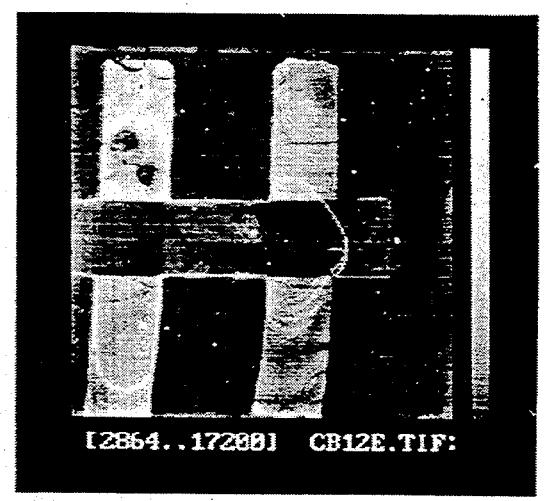
FIG. 10b presents fluorescence results showing binding of Fluorescein-anti-Mouse IgG to a slide having multiple anti-ligands.
Figure 10C:
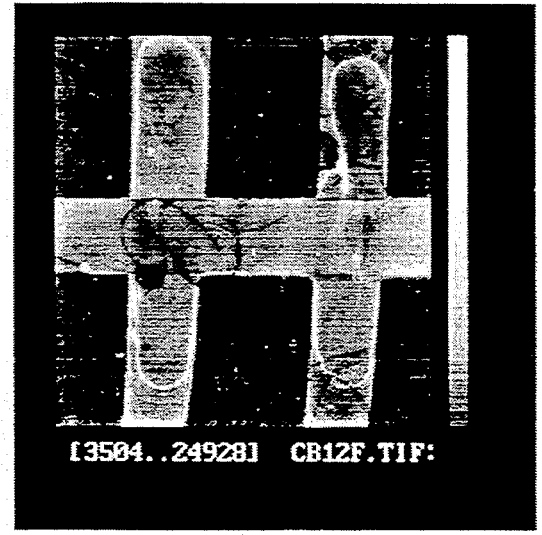
FIG. 10c presents fluorescence results showing binding of a mixture of Fluorescein-anti-Rabbit IgG and Fluorescein-anti-Mouse IgG to a slide having multiple anti-ligands.

FIG. 10 shows examples of the images obtained from the glass slide derivatized in this experiment. FIG. 10a shows the region of the glass slide treated with fluorescein-anti-Rabbit IgG. As expected, the horizontal stripe, which corresponds to the area where biotinylated Rabbit IgG bound, is intensely fluorescent indicating a high density of bound fluorescein-anti-Rabbit IgG. The vertical stripes in this region are faintly visible, which may be due to the slight cross reactivity of the secondary antibodies. FIG. 10b shows the region of the glass treated with Fluorescein-anti-Mouse IgG. Here, the vertical stripes, where Mouse IgG is bound, are fluorescent while the horizontal areas do not fluoresce appreciably. Finally, FIG. 10c shows the region treated with both secondary antibodies (fluorescein-anti-Rabbit and anti-Mouse). In this case both the vertical and horizontal stripes fluoresce, indicating a high surface density fluorescein and, therefore, of the secondary antibodies. This experiment demonstrates the spatially addressable immobilization of two different antibodies on the same surface.

What is claimed is:

1. A caged binding member compound having the formula:

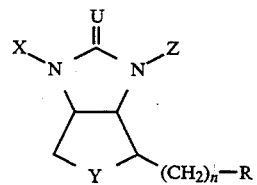

wherein X and Z are selected from the group consisting of
(a) hydrogen,
(b) oxycarbonyls of lower alkyl, aryl, and benzyl groups,
(c) a nitroveratryloxycarbonyl group,
(d) a nitropiperonyloxycarbonyl group where Z is hydrogen and R is p-nitrophenyl formate,
(e)

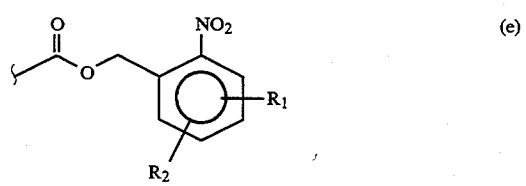

wherein $R_1$ and $R_2$ are hydrogen, lower alkyl, aryl, benzyl, halogen, hydroxyl, alkoxyl, thiol, thioether, amino, nitro, carboxyl, formate, sulfonate, formamido or phosphido groups, (f)

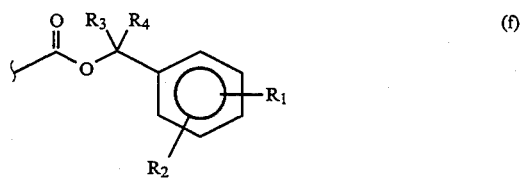

wherein $R_1$ and $R_2$ are hydrogen, lower alkyl, aryl, benzyl, pyrenyl, halogen, hydroxyl, alkoxyl, thiol, thioether, amino, nitro, carboxyl, formate, formamido or phosphido groups, and $R_3$ and $R_4$ are hydrogen, lower alkyl, aryl, benzyl, halogen, hydroxyl, alkoxyl, thiol, thioether, amino, nitro, carboxyl, formate, formamido or phosphido groups, (g)

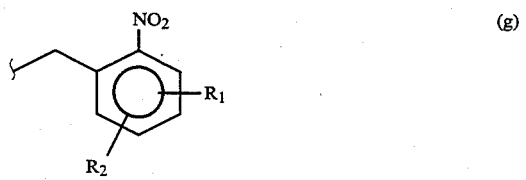

wherein $R_1$ and $R_2$ are hydrogen, lower alkyl, aryl, benzyl, halogen, hydroxyl, alkoxyl, thiol, thioether, amino, nitro, carboxyl, formate, formamido or phosphido groups, and (h)

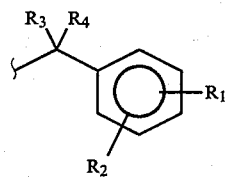

(h)

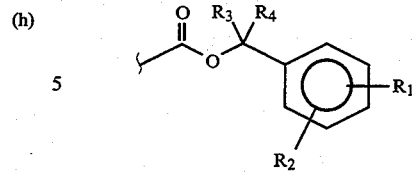

wherein $R_1$, $R_2$, $R_3$ and $R_4$ are hydrogen, lower alkyl, aryl, benzyl, halogen, hydroxyl, alkoxyl, thiol, thioether, amino, nitro, carboxyl, formate, formamido or phosphido groups, provided that when X is hydrogen, Z is not hydrogen or methyloxycarbonyl and provided that when Z is hydrogen, X is not hydrogen or methyloxycarbonyl;

R is selected from the group consisting of hydrogen, lower alkyl, aryl, carboxylate lower alkyl formate, aryl formate, methyl formate, p-nitrophenyl formate, formamide, N-alkylformamide, N-succinimidyl, hydroxyl, alkoxyl, thiol, thioether, disulfide, hydrazide and amine groups, provided that when X or Z is methyloxycarbonyl, R is not methyl formate;

U is O, S or NH;

Y is selected from the group consisting of sulfur, oxygen, methylene, carbonyl, sulfinyl and sulfonyl groups, or Y represents two hydrogens attached to the respective carbons;

n=0-7;

or acid addition salts of the compound.

2. A compound as in claim 1 wherein U is O, Y is sulfur, and n=4.

3. A compound as in claim 1 wherein one of X and Z is a nitroveratryloxycarbonyl group.

4. A compound as in claim 1 wherein one of X and Z has the formula:

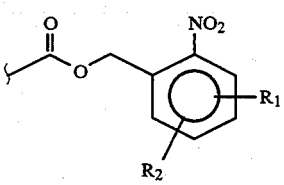

wherein $R_1$ and $R_2$ are hydrogen, lower alkyl, aryl, benzyl, halogen, hydroxyl, alkoxyl, thiol, thioether, amino, nitro, carboxyl, formate, sulfonate, formamido or phosphido groups.

5. A compound as in claim 1 wherein X is 6-nitroveratryloxycarbonyl; Z is hydrogen; and R is methyl formate.

6. A compound as in claim 1 wherein X is 6-nitroveratryloxycarbonyl; Z is hydrogen; and R is p-nitrophenyl formate.

7. A compound as in claim 1 wherein X is 6-nitropiperonyloxycarbonyl, Z is hydrogen; and R is p-nitrophenyl formate.

8. A compound as in claim 1 wherein one of X and Z is wherein $R_1$ and $R_2$ are hydrogen, lower alkyl, aryl, benzyl, pyrenyl, halogen, hydroxyl, alkoxyl, thiol, thioether, amino, nitro, carboxyl, formate, formamido or phosphido groups, and $R_3$ and $R_4$ are hydrogen, lower alkyl, aryl, benzyl, halogen, hydroxyl, alkoxyl, thiol, thioether, amino, nitro, carboxyl, formate, formamido or phosphido groups.

9. A caged binding member compound having the formula selected from the group consisting of:

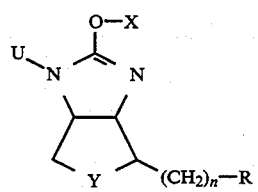

and

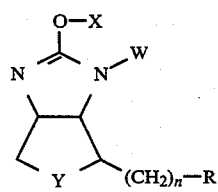

wherein X is selected from the group consisting of
(a) hydrogen,
(b) lower alkyl,
(c) aryl,
(d) benzyl,
(e) substituted benzyl selected from the group consisting of

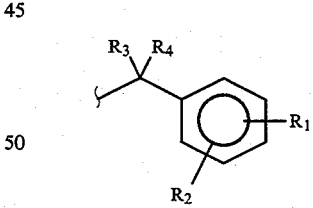

wherein $R_1$, $R_2$, $R_3$ and $R_4$ are selected from the group consisting of hydrogen, lower alkyl, aryl, benzyl, halogen, hydroxyl, alkoxyl, thiol, thioether, amino, nitro, carboxyl, formate, formamido and phosphido groups provided that $R_1$, $R_2$, $R_3$ and $R_4$ are not all hydrogen, and (ii)

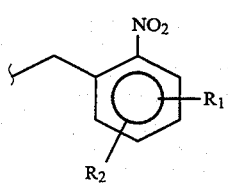

wherein R₁ and R₂ are selected from the group consisting of hydrogen, lower alkyl, aryl, benzyl, halogen, hydroxyl, alkoxyl, thiol, thioether, amino, nitro, carboxyl, formate, formamido and phosphido groups.
(f) nitroveratryl,
(g) 6-nitroveratryl,
(h) 6-nitroveratryloxycarbonyl, and
(i) 6-nitropiperonyloxycarbonyl where U or W is hydrogen;
U and W are selected from the group consisting of hydrogen, lower alkyl, aryl, benzyl and substituted benzyl selected from the group consisting of

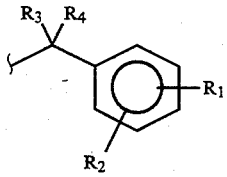

(i)

wherein R₁, R₂, R₃ and R₄ are selected from the group consisting of hydrogen, lower alkyl, aryl, benzyl, halogen, hydroxyl, alkoxyl, thiol, thioether, amino, nitro, carboxyl, formate, formamido and phosphido groups provided that R₁, R₂, R₃ and R₄ are not all hydrogen, and

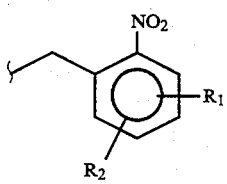

(ii)

wherein R₁ and R₂ are selected from the group consisting of hydrogen, lower alkyl, aryl, benzyl, halogen, hydroxyl, alkoxyl, thiol, thioether, amino, nitro, carboxyl, formate, formamido and phosphido groups, provided that only one of U or W is present;
R is selected from the group consisting of hydrogen, lower alkyl, aryl, carboxylate, alkyl formate, aryl formate, formamide, N-alkyl formamide, N-succinimidyl, hydroxyl, alkoxyl, thiol, thioether, disulfide, hydrazide and amine groups;
Y is selected from the group consisting of sulfur, oxygen, methylene, carbonyl, sulfinyl and sulfonyl groups, or Y represents two hydrogens attached to the respective carbons; and n=0–7; or acid addition salts of the compound.

10. A compound as in claim 9 wherein Y is sulfur and n=4.

11. A compound as in claim 9 wherein one of X, U or W has the formula:

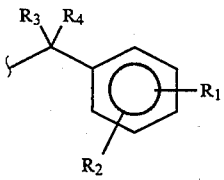

wherein R₁, R₂, R₃ and R₄ are selected from the group consisting of hydrogen, lower alkyl, aryl, benzyl, halogen, hydroxyl, alkoxyl, thiol, thioether, amino, nitro, carboxyl, formate, formamido and phosphido groups provided that R₁, R₂, R₄ are not all hydrogen.

12. A compound as in claim 11 wherein R₁ and R₂ are methoxy.

13. A compound as in claim 11 wherein R₃ and R₄ are methyl.

14. A compound as in claim 9 wherein X is a nitroveratryl group.

15. A compound as in claim 9, wherein X has the formula:

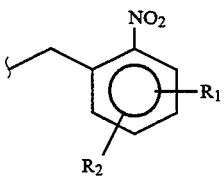

wherein R₁ and R₂ are selected from the group consisting of hydrogen, lower alkyl, aryl, benzyl, halogen, hydroxyl, alkoxyl, thiol, thioether, amino, nitro, carboxyl, formate, formamido and phosphido groups.

16. A compound as in claim 9 wherein X is 6-nitroveratryl; U or W is hydrogen: and R is methyl formate.

17. A compound as in claim 9 wherein X is 6-nitroveratryloxycarbonyl hydrogen; and R is p-nitrophenyl formate.

18. A compound as in claim 9 wherein X is 6-nitropiperonyloxycarbonyl and U or W is hydrogen.

19. A compound as in claim 9 wherein X is a substituted benzyl group, and R is methyl formate or p-nitrophenyl formate.

20. A compound as in claim 8 wherein R₁ and R₂ are methoxy.

21. A compound as in claim 8 wherein R₃ and R₄ are methyl.

* * * * *